(12) United States Patent
Dzioba

(10) Patent No.: US 10,751,197 B2
(45) Date of Patent: Aug. 25, 2020

(54) MOBILE CAGE SYSTEM FOR RESTORING MOTION KINEMATICS OF THE SPINE

(71) Applicant: Robert B. Dzioba, Tucson, AZ (US)

(72) Inventor: Robert B. Dzioba, Tucson, AZ (US)

( * ) Notice: Subject to any disclaimer, the term of this patent is extended or adjusted under 35 U.S.C. 154(b) by 0 days.

(21) Appl. No.: 16/376,817

(22) Filed: Apr. 5, 2019

(65) Prior Publication Data

US 2019/0231550 A1 Aug. 1, 2019

Related U.S. Application Data

(63) Continuation-in-part of application No. 15/863,426, filed on Jan. 5, 2018, now Pat. No. 10,307,263, and a continuation-in-part of application No. PCT/US2018/023097, filed on Mar. 19, 2018, which is a continuation of application No. 15/863,426, filed on Jan. 5, 2018, now Pat. No. 10,307,263.

(60) Provisional application No. 62/481,258, filed on Apr. 4, 2017.

(51) Int. Cl.
*A61F 2/44* (2006.01)
*A61F 2/30* (2006.01)

(52) U.S. Cl.
CPC ........ *A61F 2/4425* (2013.01); *A61F 2/30771* (2013.01); *A61F 2002/3092* (2013.01); *A61F 2002/30125* (2013.01); *A61F 2002/30153* (2013.01); *A61F 2002/30242* (2013.01); *A61F 2002/30281* (2013.01); *A61F 2002/30331* (2013.01); *A61F 2002/30462* (2013.01); *A61F 2002/30654* (2013.01); *A61F 2002/30665* (2013.01); *A61F 2002/30769* (2013.01); *A61F 2002/30784* (2013.01); *A61F 2002/30827* (2013.01); *A61F 2002/30904* (2013.01); *A61F 2002/443* (2013.01); *A61F 2002/448* (2013.01); *A61F 2310/00023* (2013.01); *A61F 2310/00029* (2013.01)

(58) Field of Classification Search
CPC ..... A61F 2/442; A61F 2/4425; A61F 2/30771
See application file for complete search history.

(56) References Cited

U.S. PATENT DOCUMENTS

| 5,947,971 A | 9/1999 | Kuslich et al. |
| 8,709,094 B2 | 4/2014 | Stad et al. |
| 2003/0204261 A1* | 10/2003 | Eisermann ............ A61F 2/4425 623/17.14 |

(Continued)

OTHER PUBLICATIONS

J.-C. Wu, T.-H. Tu, and P. V. Mummaneni, "Spinal arthroplasty: differences between the cervical and lumbar spine," World Neurosurgery, vol. 78, No. 3-4, pp. 245-246, 2012.

(Continued)

*Primary Examiner* — Si Ming Ku
(74) *Attorney, Agent, or Firm* — Nguyen Tarbet

(57) ABSTRACT

A mobile cage system for restoring motion kinematics of the spine featuring a pair of opposing caps that form a cavity and a nucleus disposed in the cavity. The system allows for motion of the caps relative to the nucleus. The mobile cage system provides sufficient support so as to eliminate the need for incorporation of a metal plate or rod and pedicle screws that may be used for spinal fusions. The mobile cage system of the present invention also prevents vertical collapse of the vertebrae and complete bone fusion, and the mobile cage system helps preserve intervertebral motion of the spine.

13 Claims, 7 Drawing Sheets

(56) References Cited

U.S. PATENT DOCUMENTS

2008/0114453 A1* 5/2008 Francis ............... A61F 2/4425
623/17.14
2011/0137421 A1 6/2011 Hansell et al.

OTHER PUBLICATIONS https://www.hcup-us.ahrq.gov/reports/statbriefs/sb186-Operating-Room-Procedures-United-States-2012.jsp.

Rajaee, S; Kanim, L.; Delamarter, R B; Bae H W; A Careful Analysis of Trends in Spinal Fusion in the United States from 1998 to 2008. Poster No. 642, ORS 2011 Annual Meeting.

Pahlavan S, Berven S, Bederman S, "Variation in Costs of Spinal Implants in United States Academic Medical Centers" Spine 41(6):515-521, Mar. 2016.

Jau-Ching Wu, Patrick C. Hsieh, Praveen V. Mummaneni, and Michael Y. Wang, "Spinal Motion Preservation Surgery", BioMed Research International, vol. 2015, Article ID 372502, 3 pages.

Oliveira et al., Porous Structure Characterization in Titanium Coating for Surgical Implants, Materials Research, vol. 5, No. 3, 269-273, 2002.

Shareghi et al. Wear of Vitamin E-Infused Highly Cross-Linked Polyethylene at Five Years , J Bone Joint Surg Am, 2017, 99:1447-52.

International Search Report issued in PCT Application No. PCT/US18/23097, dated May 31, 2018.

* cited by examiner $a < b$       $a = b$       $a > b$

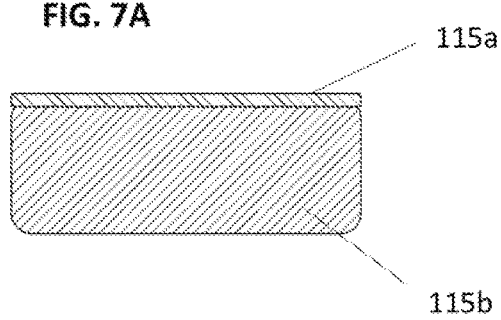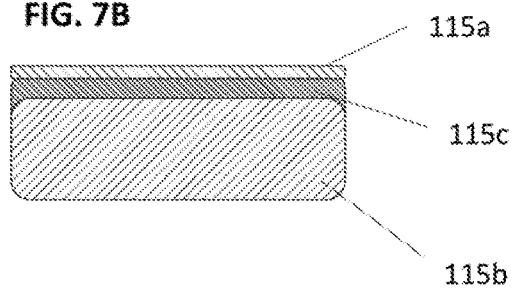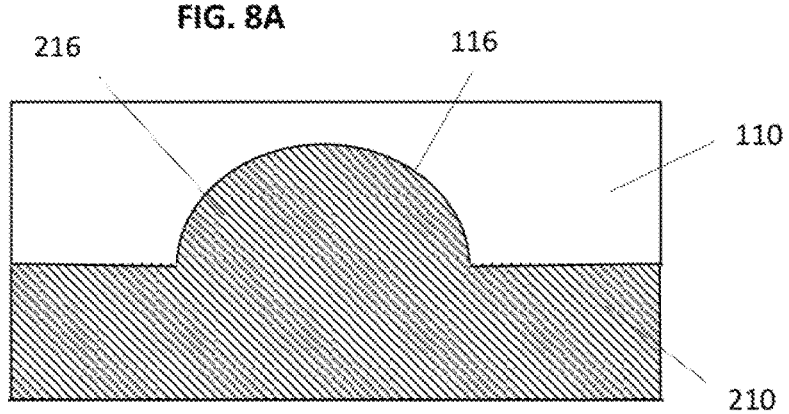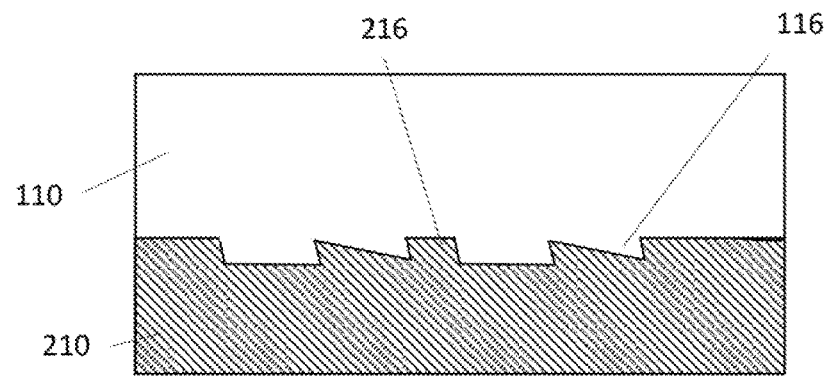

FIG. 9
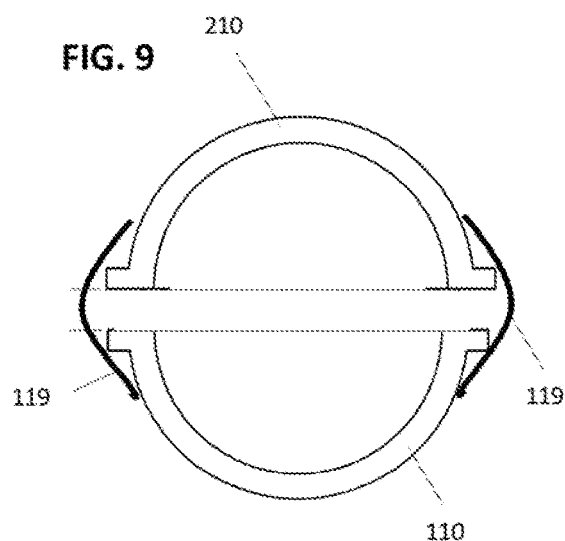
FIG. 10
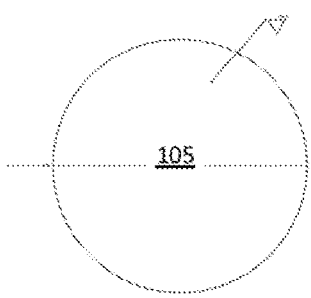
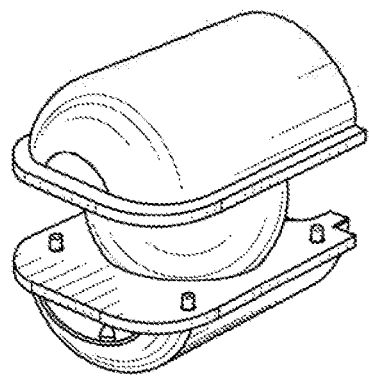
FIG. 11A
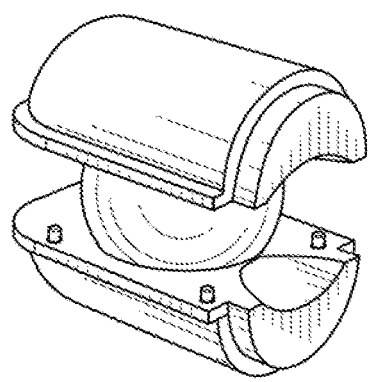
FIG. 11B
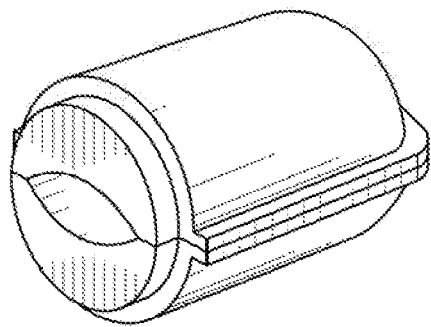
FIG. 11C
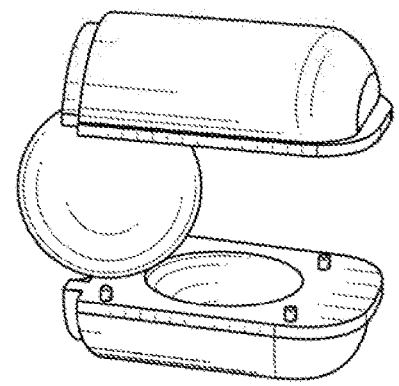
FIG. 11D

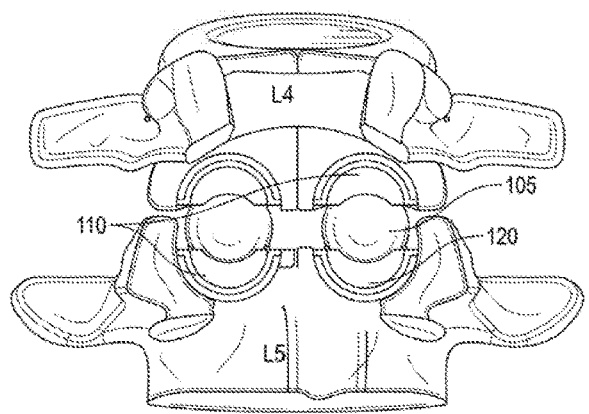
FIG. 12A
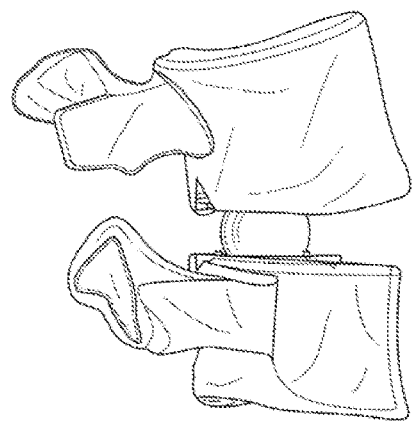
FIG. 12B
FIG. 13
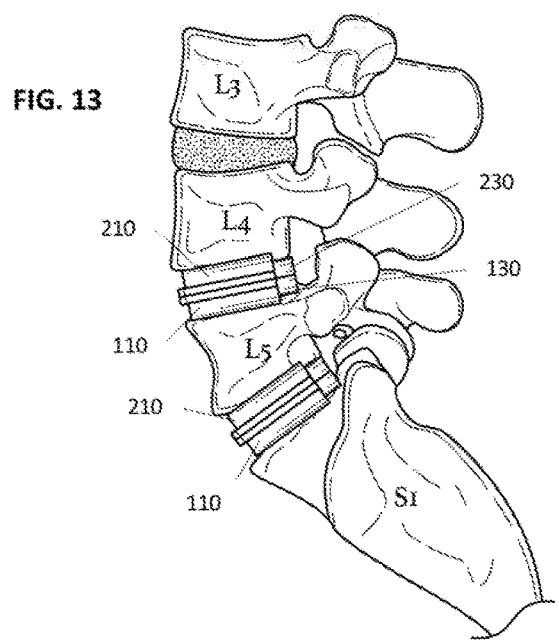
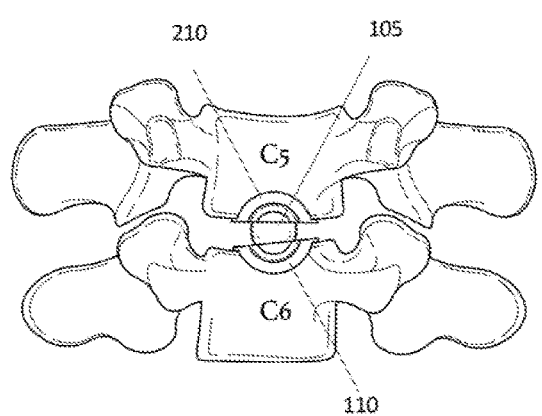
FIG. 14A
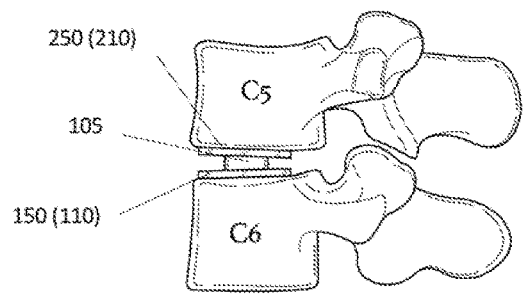
FIG. 14B

MOBILE CAGE SYSTEM FOR RESTORING MOTION KINEMATICS OF THE SPINE

CROSS REFERENCE

This application is a continuation-in-part and claims benefit of U.S. patent application Ser. No. 15/863,426 filed on Jan. 5, 2018, which is a non-provisional, and benefit of U.S. Patent Application No. 62/481,258 filed Apr. 4, 2017, the specifications of which are incorporated herein in their entirety by reference.

This application is a continuation-in-part and claims benefit of PCT Application No. PCT/US18/23097, filed Mar. 19, 2018, which claims benefit of U.S. patent application Ser. No. 15/863,426 filed on Jan. 5, 2018 and U.S. Patent Application No. 62/481,258 filed Apr. 4, 2017, the specifications of which are incorporated herein in their entirety by reference.

FIELD OF THE INVENTION

The present invention relates to methods and devices for restoring or preserving motion kinematics of the spine, for example a device for positioning in a spinal disc space (e.g., via posterior or lateral insertion), more particularly a mobile cage system for providing sufficient support to eliminate the need for fusion techniques and for restoring or preserving motion kinematics of the spine. The present invention is not limited to applications for restoring or preserving motion kinematics of the spine. For example, the mobile cage system of the present invention may be used for treating or ameliorating other spinal conditions such as scoliosis, kyphosis, hyperlordosis, or other deformities.

BACKGROUND OF THE INVENTION

The vertebral column provides a strong, yet mobile central axis for the skeleton. The vertebral column is composed of a series of 31 separate bones known as vertebrae: seven cervical or neck vertebrae, 12 thoracic vertebrae, five lumbar vertebrae, five fused vertebrae that make up the sacrum, and two coccygeal vertebrae. Each vertebra is composed of a body anteriorly and a neural arch posteriorly. The arch encloses an opening, the vertebral foramen, which helps to form a canal in which the spinal cord is housed. Protruding from the posterior extreme of each neural arch is a spinous process and extending from the lateral edges of each arch are transverse processes. These bony elements serve as important sites of attachment of deep back muscles. The parts of the neural arch between the spinous and transverse processes are known as the laminae, and the parts of the arch between the transverse processes and the body are the pedicles. At the point where the laminae and pedicles meet, each vertebra contains two superior articular facets and two inferior articular facets. The superior articular facets form articulations, which are synovial joints, with the two inferior articular facets of the vertebra immediately above (or the skull, in the case of the first cervical vertebra). The pedicle of each vertebra is notched at its superior and inferior edges. Together the notches from two contiguous vertebra form an opening, the intervertebral foramen, through which spinal nerves pass. Differences in vertebral structure exist between the different spinal regions. For example, massive bodies and robust spinous and transverse processes characterize lumbar vertebrae. Lumbar vertebrae also contain small mammillary and accessory processes on their bodies. These bony protuberances are sites of attachment of deep back muscles.

In addition to various types of ligaments, such as supraspinous ligaments, interspinous ligaments, intertransverse ligaments, and ligamentum flavum, the bodies of adjacent vertebra are connected by cartilaginous joints known as intervertebral discs. Intervertebral discs are a fundamental component of the spinal motion segment, providing cushioning and flexibility. Each disc is composed of a central core of gelatinous material, known as the nucleus pulposus, and a surrounding series of fibrous rings known as the annulus fibrosis. In some individuals, the nucleus pulposus is forced out of the disc, or is herniated, which then affects the spinal nerves. Two ligaments connect the vertebral bodies anteriorly and posteriorly: the anterior longitudinal ligament, which is strong and robust throughout, and the posterior longitudinal ligament, which becomes thin and narrow in the lumbar region. This change in structure of the posterior longitudinal ligament is part of the reason that a majority of disc herniations occur posteriorly in the lumbar region.

The spinal cord begins tat the level of the foramen magnum of the skull and ends at the level of the L1-L2 intervertebral joint. There it tapers to a cone-shaped ending known as the conus medullaris. All of the roots of the spinal nerves from L2 to the lowest coccygeal nerve pass caudal to the conus medullaris to exit at their respective intervertebral foramina. This mass of spinal roots within the spinal canal (in the subarachnoid space) is known as the cauda equina.

Degenerative disc disease, spinal stenosis, and posterior protrusion of a herniated lower lumbar intervertebral disc are diseases or conditions that can compress lumbar nerve roots, causing severe pain and/or physical dysfunction.

For conditions such as degenerative disc disease, spinal fusion is a surgical procedure designed to immobilize motion of the painful vertebral segments with the expectation of alleviation of pain associated with the degenerative disc disease. Spinal fusion may involve the removal of the intervertebral disc from the space between two vertebrae and subsequent incorporation of a cage (e.g., a rigid cage) into that space. In some cases, the rigid cage is hollow or a bone graft (e.g., autologous bone, synthetic bone) and/or other components are incorporated into the cage. The bone graft allows for bone growth between the two vertebrae (and through the cage), creating a bone fusion that inhibits motion. These rigid cages require support; hence spinal fusions also typically involve the insertion of pedicle screws and a metal rod or plate. For spinal stenosis, decompressive laminectomy, which features the removal of bone or tissue that causes narrowing of the spinal canal or squeezing of the spinal nerve roots, may be used to alleviate pain. Spinal fusion may be used as a stabilizing procedure following decompressive laminectomies.

The most commonly employed spinal fusion surgical techniques include: (i) posterior lumbar interbody fusion (PLIF), transforaminal lumbar interbody fusion (TLIF), extreme lateral interbody fusion (XLIF), and anterior lumbar interbody fusion (ALIF). PLFI is a procedure done from the back and includes removing the disc between two vertebrae and inserting bone into the space created between the two vertebral bodies. Currently as part of the fusion procedure and in most surgical cases, bone is packed into small metal or carbon fiber containers called cages that act as additional support for the graft or the verterbral bodies. TLIF is similar to the PLIF as this procedure is also done from the back of the spine. However, the surgeon will make incisions that line up with the foramen vs. the middle of the back (as is done in a PLIF procedure). XLIF is an interbody fusion in which the approach is from the side. ALIF is done from the front and includes removing the disc between two vertebrae and inserting bone into the space created between the two vertebral bodies.

While fusion is the most common type of procedure performed on the lumbar region, there are risks associated with this approach: unnatural changes of motion pattern by immobilization; increased frequency of degeneration of adjacent segments; compensatory hypermobility of adjacent segments; and increased rate of spondylolysis (stress fracture) and spondylolisthesis (instability) of adjacent segments.

The only currently approved motion preservation solution for the lumbar region of the spine is disc arthroplasty (disc replacement). The challenge with disc arthroplasty is that the procedure must be done with an anterior approach, which is risky and complex. In addition, disc arthroplasty addresses the source of pain for a very small percentage of patients that present with lumbar spine pain. Prior to undertaking surgery for disc arthroplasty, a physician typically will utilize various tools such as X-ray, MRI and discograms to attempt to confirm that the source of the pain is actually attributable to the disc and not due to some other element of the spine. Confirming that the source of pain is the disc is a crucial indication since the anterior approach required for a disc arthroplasty involves additional risk to the patient due to the extensive nature of the surgery itself. Proving that a patient's spine pain is in fact due to disc failure is challenging and controversial and as a result, surgeons typically opt for other less risky procedures to alleviate the patient's pain.

The present invention features a mobile cage system for restoring motion kinematics of the spine that can be implanted via a posterior or lateral approach. The mobile cage system of the present invention provides sufficient support so as to eliminate the need for incorporation of a metal plate or rod and pedicle screws for enhanced stability. The mobile cage system of the present invention also prevents vertical collapse of the vertebrae and complete bone fusion; thus, the mobile cage system helps preserve intervertebral motion of the spine. Without wishing to limit the present invention to any theory or mechanism, it is believed that preservation of intervertebral motion of the spine is beneficial because motion-limiting methods, such as fusions, often result in degenerated arthritic or osteoporotic bone in adjacent vertebral area (e.g., adjacent segment disease). The present invention also eliminates the need for bone graft harvesting. Surgical procedures using the mobile cage system of the present invention may be easier and faster than spinal fusion surgeries.

As previously discussed, the mobile cage system of the present invention may be used for other applications such as but not limited to treating or ameliorating spinal conditions such as scoliosis, kyphosis, hyperlordosis, or other deformities.

The present invention is not limited to the specific surgical approaches or lumbar spaces described herein. For example, for low lumbar vertebrae, the system of the present invention may be implanted via a posterior or via a transforaminal approach. For mid lumbar vertebrae, a posterior or lateral approach may be used. For thoracic vertebrae, an anterior approach may be used. In some embodiments, the system is implanted unilaterally, e.g., a single cage is placed on one side (e.g., to the left of the cauda equina, to the right of the cauda equina). This approach may be useful for treatment of diseases such as scoliosis as described above.

The mobile cage systems of the present invention may be used above or below a spinal fusion (e.g., a short spinal fusion).

SUMMARY OF THE INVENTION

The present invention provides mobile cage systems for restoring motion kinematics of the spine. In certain embodiments, the mobile cage systems herein may be used for a posterior approach in an intervertebral disc space. In certain embodiments, the mobile cage systems herein may be used for a lateral approach in an intervertebral disc space. In certain embodiments, the mobile cage systems herein may be used for treating or ameliorating a spinal condition such as scoliosis.

The present invention features mobile cage systems. The systems comprise a pair of opposing caps, e.g., a first cap and a second cap. In some embodiments, the first cap comprises a first cap first end, a first cap second end opposite the first cap first end, a first cap inner surface, and a first cap outer surface. The first cap outer surface is a curved face of a semi-cylindrical shape oriented along a longitudinal axis. At least a portion of the first cap outer surface is porous. The first cap further comprises a first cap concave indentation disposed in the first cap inner surface, wherein the first cap concave indentation is partial-hemispherical or partial-ellipsoidal. The first cap concave indentation is for accepting a spherical nucleus that can rotate therein. The first cap further comprises a first cap loading indentation disposed in the first cap inner surface, wherein the first cap loading indentation has a first end at the first cap second end and extends to a second end near the first cap concave indentation. The first cap loading indentation may have a shape in a form of a quarter ellipsoid wherein the first end of the first cap loading indentation has a width that is larger than that of the second end (the shape may be non-cylindrical). The first cap loading indentation is not limited to this particular shape. The first cap further comprises a first peak disposed between the first cap concave indentation and the second end of the first cap loading indentation. The first peak prevents a spherical nucleus positioned in the first cap concave indentation from being dislodged via the first cap loading indentation.

In some embodiments, the second cap comprises a second cap first end, a second cap second end opposite the second cap first end, a second cap inner surface, and a second cap outer surface. The second cap outer surface is a curved face of a semi-cylindrical shape oriented along a longitudinal axis. At least a portion of the second cap outer surface is porous. The second cap further comprises a second cap concave indentation disposed in the second cap inner surface. The second cap concave indentation is partial-hemispherical or partial-ellipsoidal. The second cap concave indentation is for accepting a spherical nucleus that can rotate therein. The second cap further comprises a second cap loading indentation disposed in the second cap inner surface. The second cap loading indentation has a first end at the first cap second end and extends to a second end near the second cap concave indentation. The second cap loading indentation has a non-cylindrical shape in a form of a quarter ellipsoid wherein the first end of the second cap loading indentation has a width that is larger than that of the second end. The second cap further comprises a second peak disposed between the second cap concave indentation and the second end of the second cap loading indentation. The second peak prevents a spherical nucleus positioned in the second cap concave indentation from being dislodged via the second cap loading indentation.

The pair of caps can move between (i) a collapsed position for insertion into an intervertebral space via a posterior or lateral surgical method and (ii) a distracted position for insertion of a spherical nucleus between the concave indentations. In the collapsed position the first cap inner surface is in contact with the second cap inner surface and the loading indentations together form a hemi-ellipsoid cavity, and in the distracted position the inner surfaces of the caps are a distance apart so that the loading indentations form a cradle and can temporarily hold and align a spherical nucleus for the purpose of inserting the spherical nucleus in between the concave indentations.

The mobile cage system is for posterior insertion in an intervertebral disc space. In some embodiments, the system is for lateral insertion in an intervertebral disc space.

In some embodiments, the first peak has a top edge that is on a same plane as a top edge of the first cap concave indentation. In some embodiments, the second peak has a top edge that is on a same plane as a top edge of the second cap concave indentation. In some embodiments, the first peak has a top edge that is on a same plane as the first cap inner surface. In some embodiments, the second peak has a top edge that is on a same plane as the second cap inner surface.

In some embodiments, the first cap concave indentation and second cap concave indentation are hemi-elliptical in shape. In some embodiments, the first cap concave indentation and second cap concave indentation are not complete hemispherical indentations to allow exposure of a portion of a spherical nucleus therein between the concave indentations and to allow rotation of the caps about the spherical nucleus therein.

In some embodiments, the system further comprises a first cap ridge disposed along at least a portion of the first cap outer surface of the first cap and a second cap ridge disposed along at least a portion of the second cap outer surface of the second cap, the ridges function to prevent subsidence of the caps. In some embodiments, the first cap ridge is flush with the first cap inner surface of the first cap, and the second cap ridge is flush with the second cap inner surface of the second cap.

In some embodiments, the system further comprises an attachment mechanism for temporarily securing the caps in the collapsed position. In some embodiments, the attachment mechanism comprises a peg disposed on the first cap inner surface of the first cap and an opposing hole disposed on the second cap inner surface of the second cap, wherein the peg and hole engage when the caps are in the collapsed position. In some embodiments, the attachment mechanism comprises bone wax disposed on the first cap inner surface and second cap inner surface. In some embodiments, the system further comprises a first cap connecting component disposed on the first cap second end of the first cap and a second cap connecting component disposed on the second cap second end of the second cap, the first cap connecting component is shaped to engage a surgical tool that hold the caps together in the collapsed position.

In some embodiments, the system further comprises a spherical nucleus insertable between the first cap concave indentation and second cap concave indentation, the system allows for motion of at least one cap) relative to the nucleus when the nucleus is between the cap concave indentations. In some embodiments, the loading indentations help prevent the spherical nucleus from becoming dislodged from the concave indentations. In some embodiments, the spherical nucleus is constructed from a material comprising high density polyethylene (HDP) or ultra-high molecular weight polyethylene (UHMPE).

The present invention also features a mobile cage system for performing the methods herein, e.g., for a method of treating degenerative disc disease or spinal stenosis in a spine of a patient in need thereof (via a posterior surgical approach wherein the mobile cage system is implanted between a first vertebra and a second vertebra). The mobile cage system used in these methods features the mobile system described herein.

In some embodiments, the method of treating degenerative disc disease or spinal stenosis via a posterior surgical approach comprises: performing a decompression by (i) positioning the patient in a prone position; (ii) making a midline incision over appropriate spinous processes; (iii) retracting muscles; (iv) removing lamina; and (v) retracting cauda equina; separating the first vertebra from the second vertebra using a distractor; removing at least a portion of a disc between the first vertebra and second vertebra; reaming an end plate of the first vertebra and an end plate of the second vertebra to create a channel for accepting the mobile cage system, wherein reaming retains at least a portion of the end plate of the first vertebra and the end plate of the second vertebra; inserting the mobile cage system in a collapsed position into the channel formed by reaming; inserting a nucleus in between the concave indentations of the caps by distracting the mobile cage, cradling the nucleus in between the loading indentation, pushing the nucleus into the concave indentations of the caps, and removing distraction so the nucleus is captured by compression; wherein the nucleus separates the first cap inner surface from the second cap inner surface a certain distance and allows for motion of at least one cap relative to itself, wherein the loading indentations help prevent the nucleus from becoming dislodged from the concave indentations; and closing the patient. The mobile cage system treats or improves degenerative disc disease or spinal stenosis and helps restore, improve, or maintain kinematics of the spine of the patient. Note that reaming retains a portion of the vertebral end plates.

The present invention may used in a unilateral surgical approach and may be used to treat other diseases or conditions. For example, the present invention also features a method of treating or improving scoliosis in a spine of a patient in need thereof by implanting a mobile cage system between a first vertebra and a second vertebra via a posterior surgical approach. In some embodiments, the method comprises performing a decompression by (i) positioning the patient in a prone position; (ii) making a midline incision over appropriate spinous processes; (iii) retracting muscles; (iv) removing lamina; and (v) retracting cauda equina; separating the first vertebra from the second vertebra using a distractor; removing at least a portion of a disc between the first vertebra and second vertebra; reaming an end plate of the first vertebra and an end plate of the second vertebra to create a channel for accepting the mobile cage system, wherein reaming retains at least a portion of the end plate of the first vertebra and the end plate of the second vertebra; inserting the mobile cage system in a collapsed position into the channel formed by reaming; inserting a nucleus in between the concave indentations of the caps by distracting the mobile cage, cradling the nucleus in between the loading indentations, pushing the nucleus into the concave indentations of the caps, and removing distraction so the nucleus is captured by compression; wherein the nucleus separates the first cap inner surface from the second cap inner surface a certain distance and allows for motion of at least one cap relative to itself, wherein the loading indentations help prevent the nucleus from becoming dislodged from the concave indentations; and closing the patient. The mobile cage system treats or improves scoliosis and restores, improves, or maintains motion kinematics of the spine of the patient.

As previously discussed, at least a portion of the first cap outer surface of the first cap and at least a portion of the second cap outer surface of the second cap are porous. Bone growth does not extend from the first cap to the second cap via nucleus (the nucleus blocks bone growth from the first cap to the second cap). The caps can each fuse with a vertebral end plate.

The components of the mobile cage system may be constructed in various shapes and sizes. In certain embodiments, the nucleus is spherical. In certain embodiments, the nucleus is ellipsoidal. In certain embodiments, the concave indentations (first cap concave indentation and second cap concave indentation) are hemi-elliptical in shape. In certain embodiments, the loading indentations (first cap loading indentation and second cap loading indentation) are partial ellipsoidal, partial-hemispherical, or partial-conical in shape. In certain embodiments, the first cap and second cap are semi-cylindrical in shape when viewed from their respective first ends (first cap first end, second cap first end) or second ends (first cap second end, second cap second end). In certain embodiments, the first cap and second cap are box-shaped when viewed from their respective (first cap first end, second cap first end) or second ends (first cap second end, second cap second end). In certain embodiments, the first cap and second cap are wedge-shaped when viewed from their respective first ends (first cap first end, second cap first end) or second ends (first cap second end, second cap second end). In certain embodiments, the first cap first end and the second cap first end are flat. In certain embodiments, the first cap first end and the second cap first end are curved.

The components of the mobile cage system may be constructed from a variety of materials. For example, in some embodiments, at least a portion of the first cap inner surface and second cap inner surface is constructed from a material comprising titanium or cobalt chromium. In some embodiments, the nucleus is constructed from a material comprising high-density polyethylene (HDP) or ultra high molecular weight polyethylene (UHMPE). In some embodiments, at least a portion of the outer surface of the nucleus is cross-linked with Vitamin E.

The present invention also provides kits comprising one or more components of the mobile cage system. For example, a kit may comprise the first cap and the second cap. In certain embodiments, the kit comprises the nucleus. In certain embodiments, the kit comprises the first cap, the second cap, and the nucleus. In certain embodiments, the kit further comprises one or more surgical tools such as a tool for inserting the caps into the intervertebral space, a tool for inserting the nucleus into the inner cavity between the caps, a reamer, a tool (e.g., spreader/impactor) specially fitted for this application for spreading the vertebrae and for embedding the porous-coated caps into the cancellous bone, etc.

The present invention also provides methods of insertion or implantation of the mobile cage systems herein.

In certain embodiments, two mobile cages are implanted (bi-laterally, e.g., one to the left of the cauda equina and one to the right of the cauda equina). In certain embodiments, a single mobile cate is implanted, e.g., to the left of the cauda equina or to the right of the cauda equina.

Note that surgical procedures for implantation that may be used in according with the present invention are not limited to the procedures and methods specifically described herein. For example, in certain embodiments, the mobile cage system is inserted in a manner similar to surgical methods used in transforaminal approaches, e.g., the mobile cage of the present invention may be inserted from the side, the mobile cage of the present invention may be inserted obliquely, etc. Without wishing to limit the present invention to any theory or mechanism, it is believed that for certain circumstances (e.g., a system with a spherical nucleus), the caps do not necessarily need to be aligned with the vertebra in an anterior to posterior direction (e.g., as mentioned above, in certain embodiments, the caps can be implanted obliquely).

At least a portion of the vertebral end plate is retained after reaming. For example, in some embodiments, reaming retains from 5 to 50% of the vertebral end plates. In some embodiments, reaming retains from 20 to 60% of the vertebral end plate. In some embodiments, reaming retains from 25 to 75% of the vertebral end plate. In some embodiments, reaming retains from 30 to 90% of the vertebral end plate.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which:

FIG. 7A shows a schematic view of a cross section of a portion of a cap, wherein the cap is constructed from an outer layer and an inner layer.

FIG. 7B shows a schematic view of a cross section of a portion of a cap, wherein the cap is constructed from an outer layer, an inner layer, and a middle layer.

FIG. 8A shows a schematic view of a cross section of the caps in the collapsed position wherein a first groove engages a second groove. The schematic is not drawn to scale.

FIG. 8B shows a schematic view of a cross section of the caps in the collapsed position wherein a first groove engages a second groove. The schematic is not drawn to scale.

FIG. 9 shows a schematic view of the caps in the separated position, wherein the caps are connected via a stretchable component.

FIG. 10 shows a cross sectional view of a spherical nucleus.

FIG. 11A shows a front perspective view of the system of the present invention.

FIG. 11B shows a rear perspective view of the system of the present invention.

FIG. 11C shows a front perspective view of the system of the present invention in the collapsed position without the nucleus.

FIG. 11D shows a side perspective view of the system of the present invention, wherein the nucleus rests in the loading indentations.

FIG. 12A shows a posterior view of the lumbar/sacral spine showing posterior midline placement of mobile cages (two mobile cages) in the L4-L5 space. The mobile cages feature caps with an outer coating wherein at least a portion of the outer coating is porous for bone ingrowth and a metallic (e.g., titanium or cobalt chromium, etc.) layer that contacts the nucleus.

FIG. 12B shows a side view of the lumbar/sacral spine and mobile cages in the L4-5 space of FIG. 12A.

FIG. 13 shows a lateral TLIF approach to insertion of single mobile cages (prior to nucleus insertion) in the L4-L5 and L5-S1 spaces. Flexion-extension of spine in this configuration may occur as a result of rocking barrel roll motion. The mobile cages feature caps with an outer coating wherein at least a portion of the outer coating is porous for bone ingrowth and a metallic (e.g., titanium or cobalt chromium, etc.) layer that contacts the nucleus.

FIG. 14A and FIG. 14B show an anterior surgical approach for applications involving the cervical spine. FIG. 14A shows an anterior-posterior view of C5-C6 with placement of a single mobile cage in the disc space. FIG. 14B shows a lateral view of the C6-C6 space (of FIG. 14A) with front to back placement of a single mobile cages.

DETAILED DESCRIPTION OF THE INVENTION

The present invention features a mobile cage system (100) for restoring or preserving motion kinematics of the spine. In certain embodiments, the mobile cage system (100) is inserted via a posterior approach. In certain embodiments, the mobile cage system (100) is inserted via a lateral approach. The present invention is not limited to these surgical approaches, e.g., as described above, in certain embodiments, the mobile cages may be implanted obliquely (similar to a transforaminal approach). The mobile cage system (100) of the present invention provides sufficient support so as to eliminate the need for spinal fusion techniques, such as those shown in FIG. 2 and FIG. 3 that feature metal rods and pedicle screws, as well as cages and bone grafts that allow for complete bone fusion between vertebrae. Because of its strength and configuration, the mobile cage system (100) of the present invention preserves or restores intervertebral motion of the spine. This may help eliminate the occurrence of degenerative disc disease in adjacent vertebrae that is often seen following spinal fusions.

Briefly, the system (100) of the present invention comprises a spherical nucleus (105) disposed between two caps (110, 210). The caps (110, 210) are designed to fuse with the bones in the vertebral end plates of the vertebrae in contact (e.g., the vertebrae above and below the damaged disc or the disc being replaced. The nucleus (105) is not fixedly attached to one or both of the caps (110, 210) and provides a bearing around which relative motion can occur. Thus, motion of the caps (110, 210) relative to the spherical nucleus (105) is possible. The system (100) of the present invention does not allow for complete bone growth resulting in bone fusion. For example, the mobile cage system (100) is designed to allow for attachment of the caps (110, 210) to the vertebral end plate but block bone growth through the nucleus (105).

In certain embodiments, e.g., for cases involving a lumbar disc replacement, the system can be implanted into a patient by first inserting the caps collapsed together (in the "collapsed position") without the nucleus. Once in place in the intervertebral space, the caps can be separated from each other and the nucleus can be inserted in between the caps. The present invention is not limited to these steps for surgical implantation. For example, in a case involving cervical disc replacement, the caps and nucleus may be implanted at the same time.

Figure 1:
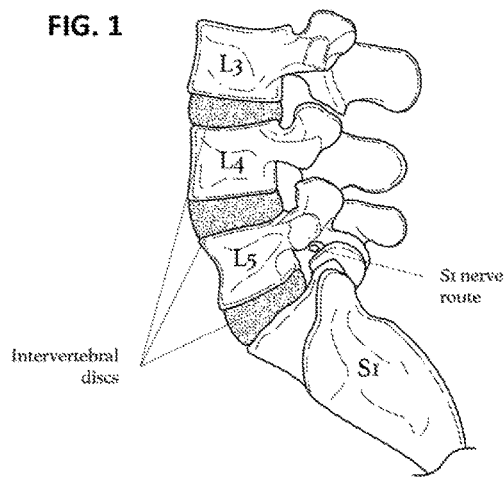
FIG. 1 shows a lateral view of a normal spine.
Figure 2:
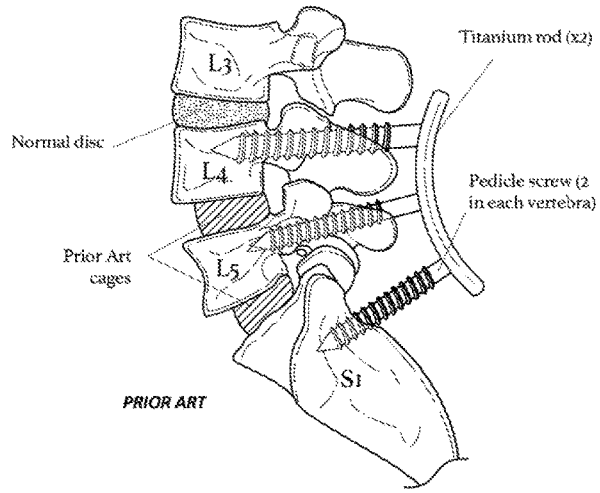
FIG. 2 shows a lateral view of L4-sacral fusion using two titanium rods, two pedicle screws, and a prior art fiber cage (rigid cage) filled with autologous bone graft inserted in the disc spaces between L4 and L5 as well as between L5 and S1. This is a common procedure in orthopedic and neuro-surgery practice.
Figure 3:
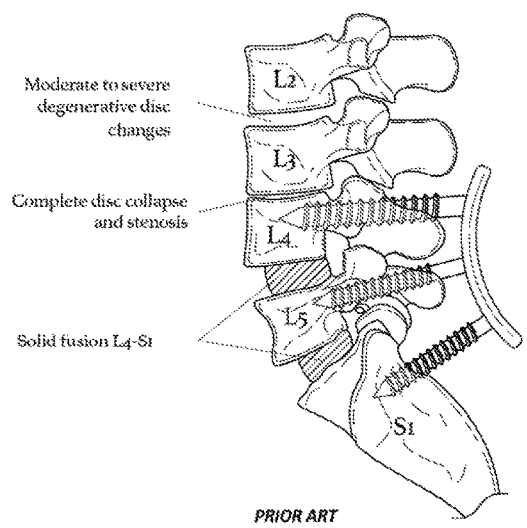
FIG. 3 shows the lateral of FIG. 2 but with moderate to severe degenerative disc changes in the L2-L3 space and complete disc collapse in the L3-L4 space, which may be expected after a certain time (e.g., 5 to 7 years) following the spinal fusion surgery shown in FIG. 2.
Figure 4:
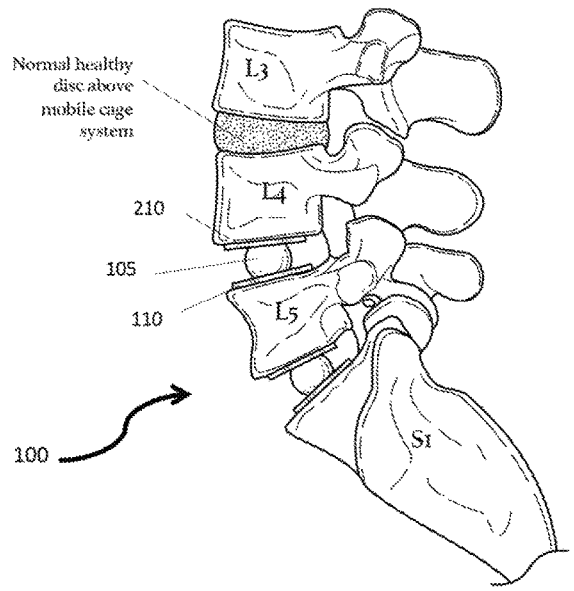
FIG. 4 shows a lateral view of the incorporation of the mobile cage system of the present invention in the L4-L5 space and L5-S1 space as an alternative to the fusion surgery shown in FIG. 2. The mobile cage system of the present invention provides enough support to eliminate the need for fusion (e.g., rod, pedicle screws, etc.). Since no fusion is performed, normal spinal motion is preserved.

FIG. 4 shows a lateral view of the incorporation of the mobile cage system of the present invention in the L4-L5 space and L5-S1 space as an alternative to the fusion surgery shown in FIG. 2. The mobile cage system of the present invention provides enough support to eliminate the need for fusion (e.g., rod, pedicle screws, etc.). Since no fusion is performed, normal spinal motion is preserved.

The components of the mobile cage system (100) of the present invention may be constructed in a variety of sizes (e.g., to accommodate varying sizes of patients, e.g., adults, children) and from a variety of materials or combinations of materials. The sizes and shapes of the components of the system (100) are such that the nucleus is contained between the caps. Without wishing to limit the present invention to any theory or mechanism, it is believed that the system of the present invention is stable in consideration of spinal biomechanics studies according to White and Panjabi (1990), which are well known to one of ordinary skill in the art. White and Panjabi have published the average range of segmental movements in a lumbar functional spinal unit (FSU). For example, the axial rotation of each of the L1-L2, L2-L3, L3-L4, and L4-L5 FSUs is 2°. The lateral flexion of each of the L1-L2, L2-L3, L3-L4, and L4-L5 FSUs is between 6°-8°. The flexion/extension of each of L1-L2, L2-L3, L3-L4, and L4-L5 FSUs is from 12°-16°.

The present invention is not limited to the dimensions or materials disclosed herein.

Components of the Mobile Cage System

Caps

Figure 5A:
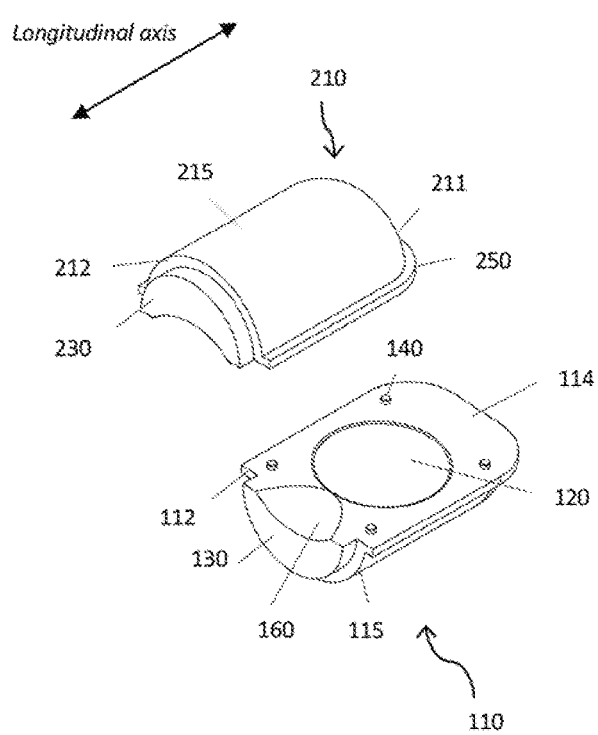
FIG. 5A shows a perspective view of the first cap and second cap of the system of the present invention. The first cap inner surface of the first cap is visible. The caps are articulated, e.g., the caps can be aligned and in contact with each other and/or connected. The caps can be separated, such as during insertion of the nucleus into the cage cavity.
Figure 5B:
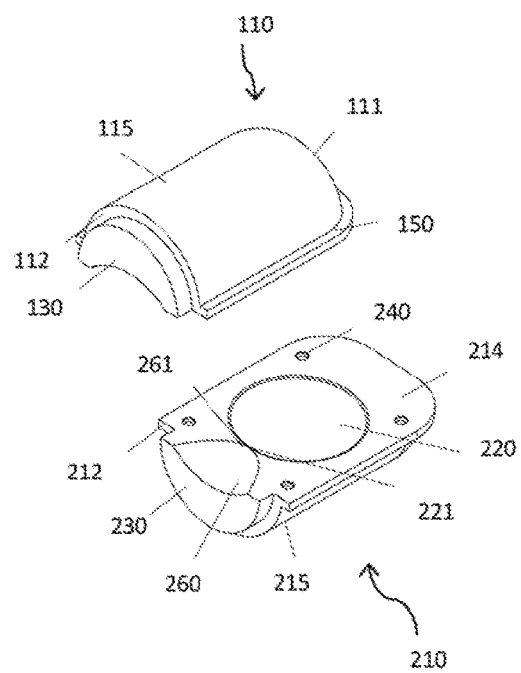
FIG. 5B shows a perspective view of the first cap and second cap of the system of the present invention. The second cap inner surface of the second cap is visible. The caps are articulated, e.g., the caps can be aligned and in contact with each other and/or connected. The caps can be separated, such as during insertion of the nucleus into the cage cavity.
Figure 5C:
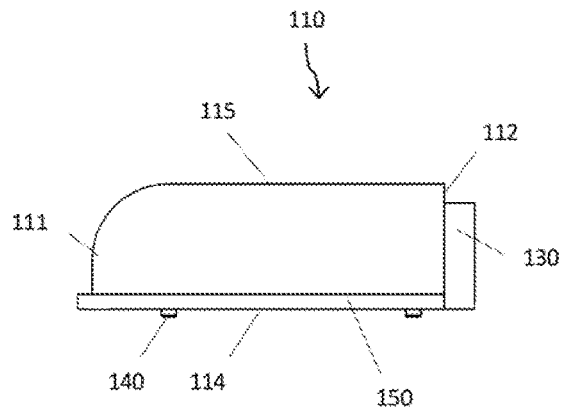
FIG. 5C shows a side view of the first cap.
Figure 5D:
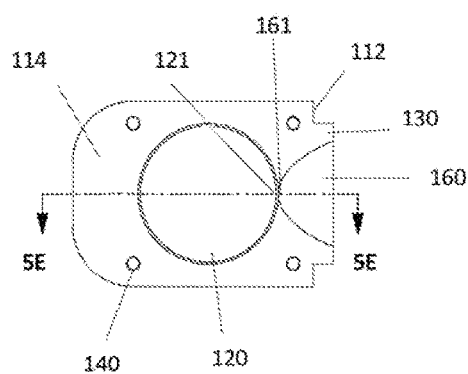
FIG. 5D shows a top view (viewing the first cap inner surface) of the first cap.
Figure 5E:
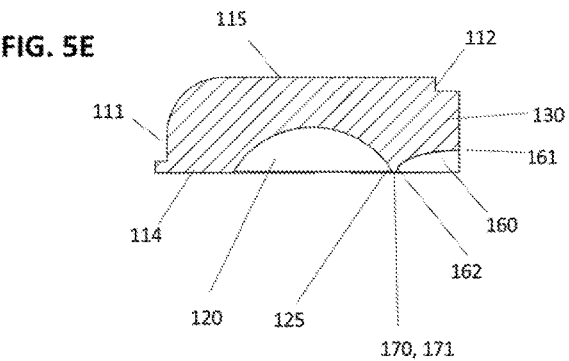
FIG. 5E shows a side cross sectional view of the first cap of FIG. 5D.
Figure 5F:
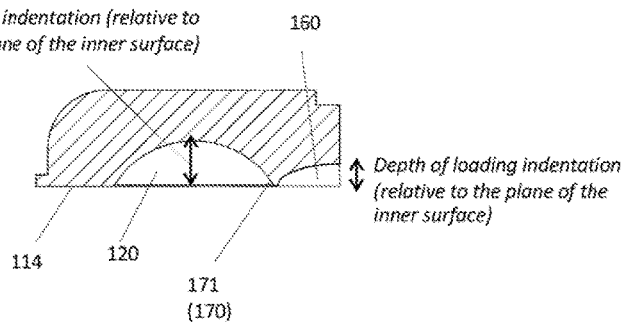
FIG. 5F shows the cap of FIG. 5E, emphasizing the peak relative to the concave indentation and the loading indentation.
Figure 5G:
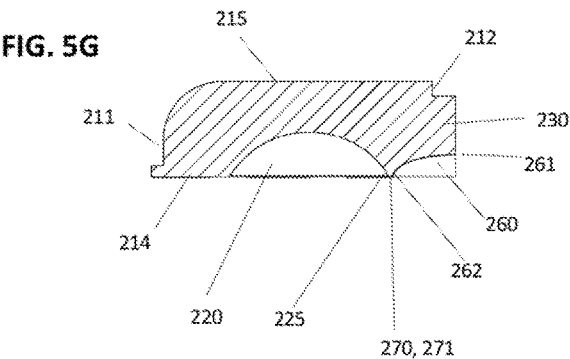
FIG. 5G shows a side cross sectional view of the second cap.
Figure 5H:
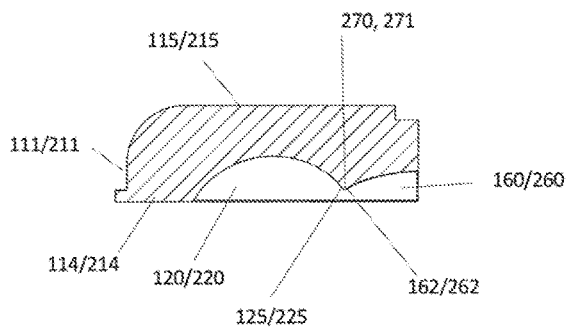
FIG. 5H shows a side cross sectional view of the second cap, wherein the second peak is slightly lower than the plane of the inner surface of the second cap.

Referring to FIG. 5A, FIG. 5B, FIG. 5C, FIG. 5D, FIG. 5E, FIG., 5F, FIG. 5G, and FIG. 5H, the mobile cage system (100) of the present invention comprises a pair of opposing caps, e.g., a first cap (110) and a second cap (210). The caps (110, 210) are articulated, e.g., the caps (110, 210) can be temporarily connected together or temporarily in contact with each other but can be separated (e.g., when the nucleus is inserted between the caps (110, 210)).

The first cap (110) has a first cap first end (111), a first cap second end (112) opposite the first cap first end (111), a first cap inner surface (114), and a first cap outer surface (115) opposite the first cap inner surface (114). The second cap (210) has a second cap first end (211), a second cap second end (212) opposite the second cap first end (211), a second cap inner surface (214), and a second cap outer surface (215) opposite the second cap inner surface (214). For the purposes of orientation, the first ends (111, 211) of the caps (110, 210) are the ends inserted first into the intervertebral space. The present invention is not limited to the shapes and configurations of the components of the systems shown herein. For example, in certain embodiments, the caps (110, 210) are generally semi-cylindrical in shape, e.g., as shown in FIG. 5A and FIG. 5B. In certain embodiments, the caps (110, 210) are generally rectangular in shape or box-shaped. In the implantation process, a particular shaped reamer is chosen based on the shape of the caps (e.g., cylindrical reamer for a cylindrical system, box-shaped reamer for a box-shaped system, etc.). In certain embodiments, the caps (110, 210) are wedge-shaped. In certain embodiments, the first ends (111, 211) of the caps (110, 210) (first cap first end, second cap first end) are curved, e.g., as shown in FIG. 5C. In certain embodiments, the first ends (111, 211) (first cap first end, second cap first end) of the caps (110, 210) are generally flat.

Figure 6A:
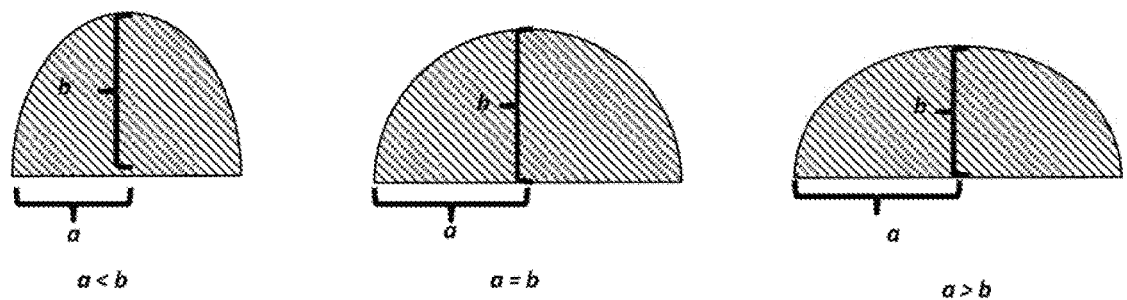
FIG. 6A shows non-limiting examples of cross-sectional views of the caps. The caps may have a semi-cylindrical or semi-ellipsoidal shape. For example, the caps have two semi-axes. In some embodiments, the semi-axes are equal (e.g., semi-cylindrical shape (middle image). In some embodiments, the cap has a semi-axis (a) that is bigger than the semi-axis (b) (right image). In some embodiments, the cap has a semi-axis (a) that is less than the semi-axis (b) (left image).

The inner surfaces (114, 214) of the caps (110, 210) are oriented to face each other, e.g., the first cap inner surface (114) faces the second cap inner surface (214). The outer surfaces (115, 215) of the caps (110, 210) are curved, e.g., as shown in FIG. 5A and FIG. 5B. In certain embodiments, the caps (110, 210) (e.g., first cap outer surface, second cap outer surface) have a cross sectional shape that is semi-cylindrical or semi-ellipsoidal. For example, referring to FIG. 6A, the cross-sections of the caps (110, 210) have two semi-axes (a) and (b). In certain embodiments, the two semi-axes (a) and (b) are equal (middle image of FIG. 6A, a semi-cylindrical shape). In certain embodiments, the semi-axes are a semi-major axis and a semi-minor axis, e.g., one axis is larger than the other. For example, the semi-axis (a) may be smaller than the semi-axis (b) (left image in FIG. 6A, a semi-ellipsoidal shape); or, the semi-axis (a) may be larger than the semi-axis (b) (right image in FIG. 6A, a semi-ellipsoidal shape).

The first cap (110) comprises a first cap concave indentation (120) in the first cap inner surface (114). The second cap (210) comprises a second cap concave indentation (220) in the second cap inner surface (214). The first cap concave indentation (120) and the second cap indentations (220) can be aligned to form a cavity (125) or nest when the caps (110, 210) are connected or in contact with each other (see FIG. 6B, left image). Without wishing to limit the present invention to any theory or mechanism, while the nucleus (105) may be spherical, the cavity (125) or nest is not limited to a spherical cavity (125). In certain embodiments, the cavity (125) or nest may be ellipsoidal in shape, e.g., the first cap concave indentation (120) and second cap concave indentation (220) are hemi-ellipsoidal in shape. Note that when the caps (110, 210) are separated a certain distance (see FIG. 6B, right image), the first cap concave indentation (120) and second cap concave indentation (220) form a space that can house a spherical nucleus (105).

Figure 6B:
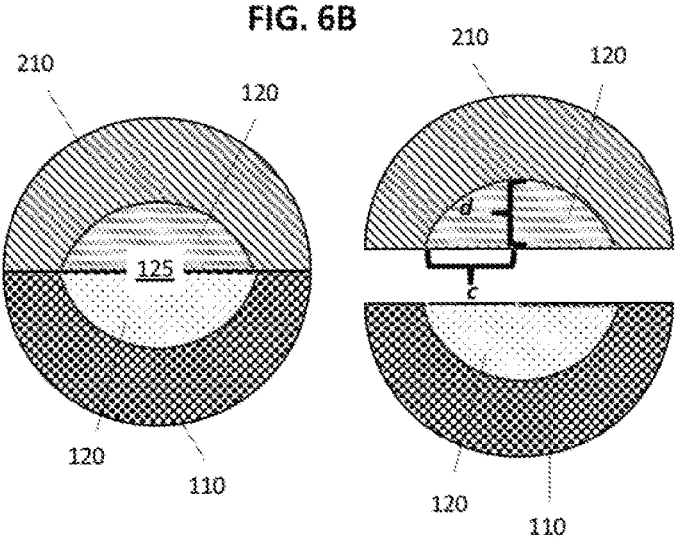
FIG. 6B shows a schematic view of a cross section of the caps in an orientation that aligns the concave indentations in the inner surfaces to form a cavity. In this example, the concave indentations are hemi-ellipsoidal and form a cavity that is ellipsoidal.

The first cap concave indentation (120) and second cap concave indentation (220) have a major axis (c) and a minor axis (d) (see FIG. 6B). The dimensions of the major and minor axes depend on the size of the nucleus used. For example, in certain embodiments, the nucleus (105) has a radius of 9 mm. In certain embodiments, the nucleus (105) has a radius of 8 mm. In certain embodiments, the nucleus (105) has a radius of 7 mm. In certain embodiments, the nucleus (105) has a radius of 6 mm. As an example, in the case of a nucleus (105) having a radius of 8 mm, in certain embodiments, the major axis (c) of the concave indentations is less than 8 mm, e.g., from 7 to 7.5 mm, from 6 to 7 mm, from 5 to 7 mm, from 4 to 7 mm, from 4 to 6 mm, from 4 to 5 mm, etc. In certain embodiments, the minor axis (d) of the concave indentations is less than 8 mm, e.g., from 7 to 7.5 mm, from 6 to 7 mm, from 5 to 7 mm, from 4 to 7 mm, from 4 to 6 mm, from 4 to 5 mm, etc. In certain embodiments, the nucleus (105) has a radius of 9 mm. In certain embodiments, the major axis (c) of the concave indentations is less than 9 mm, e.g., from 6 to 8.5 mm, from 5 to 8 mm, from 5 to 7 mm, from 4 to 7 mm, from 4 to 6 mm, from 4 to 5 mm, from 3 to 6 mm, etc. In certain embodiments, the minor axis (d) of the concave indentations is less than 9 mm, e.g., from 6 to 8.5 mm, from 5 to 8 mm, from 5 to 7 mm, from 4 to 7 mm, from 4 to 6 mm, from 4 to 5 mm, from 3 to 6 mm, etc. The present invention is not limited to the aforementioned dimensions.

In certain embodiments, the first cap concave indentation (120) and second cap concave indentation (220) are hemi-ellipsoidal in shape, wherein the hemi-ellipsoid has a minor axis (d) and two major axes, (c) and (c'), wherein (c) and (c') are different. For example, in certain embodiments, (c) is 8 mm and (c') is 9 mm. In certain embodiments, (c) is 7 mm and (c') is 8 mm. The present invention is not limited to the aforementioned dimensions of (c) and (c').

The first cap (110) may further comprise a first cap loading indentation (160) disposed in the first cap inner surface (115) at the first cap second end (112). The second cap (210) may further comprise a second cap loading indentation (260) disposed in the second cap inner surface (214) at the second cap second ends (212). The first cap loading indentation (160) and second cap loading indentation (260) allow passage of the nucleus (105) to the cavity (125), e.g., upon application of force. The first cap loading indentation (160) and second cap loading indentation (260) are designed to provide a smooth surface for the nucleus (105) so that the nucleus (105) is not scratched upon entry into the cavity (125). For example, one or more edges of the loading indentations may be smoothed, beveled, chamfered, etc. Note that once the caps (110, 210) are surgically implanted and the nucleus (105) is pushed into the cavity (125), the nucleus (105) cannot slide back through the first cap loading indentation (160) and second cap loading indentation (260). In certain embodiments, the first cap loading indentation (160) and second cap loading indentation (260) are partial-hemispherical or partial-ellipsoidal in shape.

Without wishing to limit the present invention to any theory or mechanism, it is believed that the loading indentations (160, 260) are advantageous because they also help align the nucleus prior to insertion so that it is inserted correctly. When a posterior surgical approach is used, it can be difficult to see the mobile cage system once it is implanted (e.g., in contrast to an anterior surgical approach wherein visibility can be better); thus, the loading indentations (160, 260) serve as a means of centering and immobilizing the nucleus for accurate insertion.

As an example, in certain embodiments, the first cap loading indentation (160) and second cap loading indentation (260) occupy a space that is approximately one quarter of a hemisphere. In certain embodiments, the first cap loading indentation (160) and second cap loading indentation (260) occupy a space that is approximately one quarter of an ellipsoid.

The top inner edge (161) of the first cap loading indentation (160) may be in contact with the top edge (121) of the first cap concave indentation (120). The top inner edge (261) of the second cap loading indentation (260) may be in contact with the top edge (221) of the second cap concave indentation (220). In certain embodiments, the respective top inner edges (161, 261) of the loading indentations (160, 260) may be a distance from the respective top edges (121, 221) of the concave indentations (120, 220). For example, in some embodiments, the respective top inner edges (161, 261) of the loading indentations (160, 260) (first cap loading indentation, second cap loading indentation) and the respective top edges (121, 221) of the concave indentations (120, 220) (first cap concave indentation, second cap concave indentation) are from 0.01 to 0.1 mm apart. In some embodiments, the respective top inner edges (161, 261) of the loading indentations (160, 260) and the respective top edges (121, 221) of the concave indentations (120, 220) are from 0.1 to 1 mm apart. In some embodiments, the respective top inner edges (161, 261) of the loading indentations (160, 260) and the respective top edges (121, 221) of the concave indentations (120, 220) are from 0.5 to 2 mm apart. In some embodiments, the respective top inner edges (161, 261) of the loading indentations (160, 260) and the respective top edges (121, 221) of the concave indentations (120, 220) are from 1 to 3 mm apart. In some embodiments, the respective top inner edges (161, 261) of the loading indentations (160, 260) and the respective top edges (121, 221) of the concave indentations (120, 220) are from 2 to 4 mm apart. In some embodiments, the respective top inner edges (161, 261) of the loading indentations (160, 260) and the respective top edges (121, 221) of the concave indentations (120, 220) are from 1 to 5 mm apart. In some embodiments, the respective top inner edges (161, 261) of the loading indentations (160, 260) and the respective top edges (121, 221) of the concave indentations (120, 220) are from 3 to 5 mm apart. In some embodiments, the respective top inner edges (161, 261) of the loading indentations (160, 260) and the respective top edges (121, 221) of the concave indentations (120, 220) are from 0.1 to 6 mm apart. In some embodiments, the respective top inner edges (161, 261) of the loading indentations (160, 260) and the respective top edges (121, 221) of the concave indentations (120, 220) are from 0.5 to 7 mm apart.

The loading indentations (160, 260) (first cap loading indentation, second cap loading indentation) and the concave indentations (120, 220) (first cap concave indentation, second cap concave indentation) are designed to secure the nucleus (105) in place between the caps (110, 220) to prevent the nucleus from popping out. The caps (110, 210) are designed to prevent breakage or fracturing when the nucleus (105) is inserted during surgical implantation. For example, the space between the loading indentations (160, 260) and the concave indentations (120, 220) is strong enough to resist breakage or fracturing when the nucleus is forced into the cavity and strong enough to prevent the nucleus from popping out of the cavity.

The first cap outer surface (115) of the first cap (110) and the second cap outer surface (215) of the second cap (210) are for contacting the vertebrae, e.g., the end plates of the vertebrae. The caps (110, 210) allow for bony ingrowth on the outer surfaces (115, 215) to secure the caps (110, 210) to the vertebral end plates.

The caps (110, 210) may be constructed from one or more materials. In some embodiments, the caps (110, 210) are constructed with layers of materials. For example, FIG. 7A and FIG. 7B show non-limiting examples of cross sections of the caps. In some embodiments, the first cap (110) comprises a first cap outer layer (115a) (e.g., the first cap outer surface (115)) and a first cap inner layer (115b) (e.g., the first cap inner surface 114)). In some embodiments, the second cap (210) comprises a second cap outer layer (115a) (e.g., the second cap outer surface (215)) and a second cap inner layer (115b) (e.g., the second cap inner surface 214)). In some embodiments, the caps comprise an outer layer (115a), an inner layer (115b), and one or more middle layers (115c) sandwiched between the outer layer (115a) and inner layer (115b) (see FIG. 7B). In some embodiments, more than one middle layer (e.g., a first middle layer, a second middle layer, a third middle layer, etc.) is sandwiched between the outer layer (115a) and inner layer 115b).

Porous coatings are currently the predominant approach for fixation of orthopedic implants. At least a portion of the first cap outer surface (115) and second cap outer surface (215) (e.g., outer layer (115a)) is porous (e.g., comprises a porous coating). In some embodiments, the porous outer surface (115, 215) (e.g., outer layer (115a)) of the caps (110, 210) is sprayed or etched onto a middle layer (115c) or inner layer (115b). In some embodiments, the porous outer surface (115, 215) (e.g., outer layer (115a)) of the caps (110, 210) is attached to or layered onto the middle layer (115c) or inner layer (115b). In some embodiments, the outer surface (115, 215) (e.g., outer layer (115a)) of the caps (110, 210) comprises teeth or jagged edges. The porous and/or jagged and/or toothed nature of the outer surface (115, 215) (e.g., outer layer (115a)) of the caps (110, 210) may help with attachment to the vertebral end plate when the caps are inserted during surgery. The porous and/or jagged and/or toothed nature of the outer surface (115, 215) (e.g., outer layer (115a)) may help with bony ingrowth to secure the caps to the vertebral end plates. In certain embodiments, the outer surface (115, 215) (e.g., outer layer (115a)) comprises titanium, a titanium alloy, or a combination thereof. Trabeculite™ (Tecomet) is a non-limiting example of a commercial porous medical material (mesh-like material) that may be considered for the outer surface (115, 215) (e.g., outer layer (115a)). POROCOAT® Porous Coating (DePuy Synthes), which comprises titanium-sintered beads that allow bone to affix into the porous coating, is another non-limiting example of a commercial porous material that may be considered for the outer surface. Fabrication techniques for producing titanium porous coatings (including but are not limited to powder metallurgy) are well known to one of ordinary skill in the art. Materials used to produce the porous coating (e.g., pure titanium, Ti-6Al-7Nb metallurgy rods, etc.) are also well known to one of ordinary skill in the art. See, for example, Oliveira et al., 2002, Materials Research 5(3): 269-273.

As previously discussed, in certain embodiments, at least a portion of the first cap outer surface (115) and at least a portion of the second cap outer surface (215) are porous. In certain embodiments, a portion of the caps (110, 210) is porous. For example, in some embodiments, the outer surfaces (115, 215) of the caps (110, 210) are designed such that the porous portion is just positioned on the part of the caps (110, 210) where the vertebral bone (end plate) is expected to contact the caps (110, 210). In some embodiments, the amount of porous coating depends on the shape of the caps (110, 210). In certain embodiments, the first cap first end (111) and second cap first end (211) or a portion thereof is smooth. In some embodiments, the first cap first end (111) and second cap first end (211) or a portion thereof does not comprise the porous coating.

In certain embodiments, the inner surfaces (114, 214) (e.g., inner layer (115b)) and/or middle layer (140c) are strong and substantial relative to the porous outer surface (115, 215) (e.g., outer layer (115a)). In certain embodiments, the thicknesses of the outer surfaces (115, 215) (e.g., outer layer (115a)) (porous coating) are thin relative to the thicknesses of the remainder of the cap (110, 210), e.g., thin relative to the inner surfaces (114, 214) (e.g., inner layer (115b)) or the combination of the inner surfaces (114, 214) (e.g., inner layer (115b)) and middle layers (115c).

The first cap inner surface (114) and second cap inner surface (214) or a portion thereof, e.g., the concave indentations (120, 220), may be a smooth surface, e.g., free of holes or pores or large defects. In some embodiments, the inner surface (or a portion thereof) of the caps (110, 210) is constructed from a material comprising cobalt chromium, titanium, the like, or a combination thereof. The first cap inner surface (114) and second cap inner surface (214) (e.g., inner layer (115b)) may help block bony ingrowth from extending to the nucleus (105), thereby allowing continued motion of the caps relative to the nucleus (105) and thus motion of the spine.

The caps (110, 210) may be constructed in a variety of sizes and may be constructed from a variety of materials (e.g., metal such as cobalt chromium, titanium, plastic, etc.).

In some embodiments, the cap (110, 210) is from 20 to 25 mm in length as measured from the first end (111, 211) to the second end (112, 212), e.g., the cap (110, 210) is 20 mm in length, the cap (110, 210) is 21 mm in length, the cap (110, 210) is 22 mm in length, the cap (110, 210) is 23 mm in length, the cap (110, 210) is 24 mm in length, the cap (110, 210) is 25 mm in length. In some embodiments, the cap (110, 210) is from 18 to 28 mm in length as measured from the first end (111, 211) to the second end (112, 212), e.g., the cap (110, 210) is 18 mm in length, the cap (110, 210) is 19 mm in length, the cap (110, 210) is 20 mm in length, the cap (110, 210) is 26 mm in length, the cap (110, 210) is 27 mm in length, the cap (110, 210) is 28 mm in length. In some embodiments, the cap (110, 210) is from 21 to 28 mm in length as measured from the first end (111, 211) to the second end (112, 212). In some embodiments, the cap (110, 210) is from 22 to 30 mm in length as measured from the first end (111, 211) to the second end (112, 212), e.g., the cap (110, 210) is 28 mm in length, the cap (110, 210) is 29 mm in length, the cap (110, 210) is 30 mm in length, etc.

In some embodiments, the cap (110, 210) has a length from 50 to 80% the length of the vertebral end plate. In some embodiments, the cap (110, 210) has a length from 60 to 80% the length of the vertebral end plate. In some embodiments, the cap (110, 210) has a length from 60 to 90% the length of the vertebral end plate. In some embodiments, the cap (110, 210) has a length from 70 to 80% the length of the vertebral end plate. In some embodiments, the cap (110, 210) has a length from 70 to 90% the length of the vertebral end plate. In some embodiments, the cap (110, 210) has a length from 75 to 95% the length of the vertebral end plate. In some embodiments, the cap (110, 210) has a length from 70 to 80% the length of the vertebral end plate.

In some embodiments, the cap (110, 210) has a length that is 40% the length of the vertebral end plate. In some embodiments, the cap (110, 210) has a length that is 45% the length of the vertebral end plate. In some embodiments, the cap (110, 210) has a length that is 50% the length of the vertebral end plate. In some embodiments, the cap (110, 210) has a length that is 55% the length of the vertebral end plate. In some embodiments, the cap (110, 210) has a length that is 60% the length of the vertebral end plate. In some embodiments, the cap (110, 210) has a length that is 65% the length of the vertebral end plate. In some embodiments, the cap (110, 210) has a length that is 70% the length of the vertebral end plate. In some embodiments, the cap (110, 210) has a length that is 75% the length of the vertebral end plate. In some embodiments, the cap (110, 210) has a length that is 80% the length of the vertebral end plate. In some embodiments, the cap (110, 210) has a length that is 85% the length of the vertebral end plate. In some embodiments, the cap (110, 210) has a length that is 90% the length of the vertebral end plate. In some embodiments, the cap (110, 210) has a length that is 95% the length of the vertebral end plate. In some embodiments, the cap (110, 210) has a length that is 98% the length of the vertebral end plate. In some embodiments, the cap (110, 210) has a length that is 99% the length of the vertebral end plate. In some embodiments, the cap (110, 210) has a length that is 100% the length of the vertebral end plate.

In some embodiments, the cap (110, 210) is from 5 to 10 mm in height as measured from the inner surface (114, 214) to the top edge of the outer surface (115, 215), e.g., 5 mm in height, 6 mm in height, 7 mm in height, 8 mm in height, 9 mm in height, 10 mm in height. In some embodiments, the cap (110, 210) is from 6 to 10 mm in height as measured from the inner surface (114, 214) to the top edge of the outer surface (115, 215). In some embodiments, the cap (110, 210) is from 7 to 9 mm in height as measured from the inner surface (114, 214) to the top edge of the outer surface (115, 215).

Table 1 below provides non-limiting examples of dimensions of embodiments of the system of the present invention.

TABLE 1

| Example | Nucleus Diameter (mm) | Nucleus Radius (mm) | Major Axis (c) of Concave Indentation of Cap (mm) | Minor Axis (d) of Concave Indentation of Cap (mm) | Distance Between Caps (mm) |
|---|---|---|---|---|---|
| 1 | 16 | 8 | 7.94 | 7 | 2 |
| 2 | 16 | 8 | 7.75 | 6 | 4 |
| 3 | 16 | 8 | 7.41 | 5 | 6 |
| 4 | 16 | 8 | 7.19 | 4.5 | 7 |
| 5 | 16 | 8 | 6.93 | 4 | 8 |
| 6 | 16 | 8 | 6.61 | 3.5 | 9 |
| 7 | 16 | 8 | 6.24 | 3 | 10 |
| 8 | 18 | 9 | 8.77 | 7 | 4 |
| 9 | 18 | 9 | 8.49 | 6 | 6 |
| 10 | 18 | 9 | 8.06 | 5 | 8 |
| 11 | 18 | 9 | 7.48 | 4 | 10 |
| 12 | 20 | 10 | 9.80 | 8 | 4 |
| 13 | 20 | 10 | 9.54 | 7 | 6 |
| 14 | 20 | 10 | 9.17 | 6 | 8 |
| 15 | 20 | 10 | 8.66 | 5 | 10 |

Additional Features of the Caps

The caps (110, 210) can be collapsed together (with the concave indentations (120, 220) aligned in a "collapsed position" (see FIG. 6B, left image) and be separated a distance apart in a "separated position" (see FIG. 6B, right image, FIG. 9). When the caps (110, 210) are inserted into the intervertebral space, the caps (110, 210) in the collapsed position. The caps (110, 210) are moved to the separated position, for example, by inserting the nucleus (105) into the cavity (125) formed by the concave indentations (120, 220).

In certain embodiments, no particular attachment mechanism is used to temporarily connect or secure the caps (110, 210) together in the collapsed position. In some embodiments, an external system (e.g., surgical tool used for the insertion process) keeps the caps (110, 210) in the collapsed position during insertion into the intervertebral space.

In some embodiments, the caps (110, 210) are temporarily connected in the collapsed position via an attachment mechanism integrated into the caps (110, 210). For example, in certain embodiments, as shown in FIG. 5A and FIG. 5B, a first attachment component (140) is disposed on the first cap inner surface (114) of the first cap (110) and a second attachment component (240) is disposed on the second cap inner surface (214) of the second cap (210), wherein the first attachment component (140) is adapted to engage and temporarily connect to the second attachment component (240) to secure the caps (110, 210) in the collapsed position. The embodiments shown in FIG. 5A and FIG. 5B show a peg-and-hole attachment mechanism, wherein the first attachment component (140) comprises a peg and the second attachment component (240) comprises a hole.

The present invention is not limited to a peg-and-hole attachment mechanism. Referring to FIG. 8A and FIG. 8B, which show cross sectional views of certain embodiments of caps (110, 210), in certain embodiments, the first cap (110) comprises one or more first grooves (116) disposed on the first cap inner surface (114) and the second cap (210) comprises one or more opposing second grooves (216) on the second cap inner surface (214), wherein the grooves (116, 216) help align the caps (110, 210) appropriately (e.g., with the concave indentations forming a cavity) and prevent sliding of the caps (110, 210), and/or the grooves (116, 216) help secure the caps (110, 210) in the collapsed position. In certain embodiments, the grooves (116, 216) are jagged and/or serrated, e.g., as shown in FIG. 8B. In certain embodiments, the grooves (116, 216) are smooth and/or curved, e.g., as shown in FIG. 8A.

In some embodiments, the attachment mechanism comprises a material coated between the caps (110, 210), e.g., bone wax or other biological material. In some embodiments, a stretchable component (119) is disposed on the caps (110, 210) that connect the caps (110, 210) but allow the caps (110, 210) to be separated up to a certain distance apart (see FIG. 9). The stretchable component (119) may be disposed along all or a portion of the sides of the caps (110, 210), for example. In certain embodiments, the stretchable component (119) is disposed along all or a portion of the first ends (111, 211) of the caps (110, 210). In certain embodiments, the stretchable component (119) comprises tethers or threads. In certain embodiments, the stretchable component (119) comprises films or sheets.

During surgical implantation, a joystick or other surgical tool is used to temporarily grip the caps (110, 210) (in the collapsed state) and guide the caps (110, 210) to the appropriate position in the intervertebral space. In certain embodiments, at least a portion of the first cap second end (112) of the first cap (110) comprises a first cap connecting component (130) and at least a portion of a portion of the second cap second end (112) of the second cap (210) comprises a second cap connecting component (230), the connecting components (130, 230) can engage (temporarily) the joystick or surgical tool used for inserting the caps (110, 210) into the intervertebral space. The first cap connecting component (130) may be an extension of a portion of the first cap second end (112), e.g., a portion of the first cap second end (112) extends or protrudes outwardly (see FIG. 5C). The second cap connecting component (230) may be an extension of a portion of the second cap second end (212), e.g., a portion of the second cap second end (212) extends or protrudes outwardly (see FIG. 5C). In some embodiments, the connecting components (130, 230) fit into an indentation within the surgical tool such that the surgical tool holds the caps (110, 210) together. In certain embodiments, a biological material, such as bone wax, is used in the indentation of the surgical tool to help temporarily secure the connecting components (130, 230) therein.

In certain embodiments, one or more holes (e.g., screw holes) may be disposed in the first ends (111, 211) (first cap first end, second cap first end) of the caps (external to the loading indentations (160, 260)). The holes may be used for engaging an insertion tool.

In certain embodiments, a first cap ridge (150) is disposed along at least a portion of the first cap outer surface (115) of the first cap (110), e.g., near the first cap inner surface (114) or in line with the first cap inner surface (114). A second cap ridge (250) is disposed along at least a portion of the second cap outer surface (215) of the second cap (210), e.g., near the second cap inner surface (214) or in line with the second cap inner surface (214) as shown in FIG. 5A and FIG. 5B. The first cap ridge (150) may extend along the sides of the first cap (110) or a portion of the sides of the first cap (110). The second cap ridge (250) may extend along the sides of the second caps (210) or a portion of the sides of the second cap (210). In certain embodiments, the first cap ridge (150) extends around the first cap first end (111) of the first cap (110). In certain embodiments, the second cap ridge (250) extends around the second cap first end (211) of the second cap (210). In certain embodiments, the first cap ridge (150) is disposed intermittently along the sides of the first cap (110) and/or the first cap first end (111) of the first cap (110). In certain embodiments, the second cap ridge (250) is disposed intermittently along the sides of the second cap (210) and/or the second cap first end (211) of the second cap (210).

Without wishing to limit the present invention to any theory or mechanism, it is believed that the ridges (150, 250) may help prevent subsidence of the caps (110, 210) by anchoring to the cortical end plate. For example, the cancellous bone will connect with the porous coating, but the ridge prevents the sinking of the caps (110, 210).

In certain embodiments, the ridges (150, 250) helps allow proper alignment in the intervertebral disc space.

Referring to FIG. 5E, FIG. 5F, FIG. 5G, and FIG. 5H, each cap comprises a peak (170, 270) between the respective concave indentations and the second ends of the loading indentations. For example, the first cap (110) comprises a first peak (170) disposed between the first cap concave indentation (120) and the second end (162) of the first cap loading indentation (160). The second cap (220) comprises a second peak (270) disposed between the second cap concave indentation (220) and the second end (262) of the second cap loading indentation (260).

The peaks (170, 270) are a raised surface as compared to the depths of the respective cap concave indentations (120, 220) and the depths of the respective loading indentations (160, 260). For example, as shown in FIG. 5F, the tip or top edge (171) of the first peak (170) is higher (e.g., closer to the plane of the inner surface of the cap) as compared to the depth of the first cap concave indentation (120) and the first cap loading indentation (160).

The peaks (170, 270) help prevent the nucleus from becoming dislodged from the cap concave indentations (120, 220) through the loading indentations (160, 260).

Referring to FIG. 5E and FIG. 5F, in some embodiments, the first peak (170, e.g., the top edge (171) of the first peak (170), is on the same plane as the first cap inner surface (114). Referring to FIG. 5G, in some embodiments, the second peak, e.g., the top edge (271) of the second peak (270), is on the same plane as the second cap inner surface (214). Referring to FIG. 5H, in some embodiments, the peaks (170, 270), e.g., the top edges (171, 271) of the peaks (170, 270), are slightly below the plane of the inner surface (114, 214) of the caps (110, 210). The top edges (171, 271) of the peaks (170, 270) may be a distance below the plane of the inner surface (114, 214) of the caps (110, 210), e.g., a distance between 0 to 1 mm, a distance between 0 to 2 mm, a distance between 0 to 3 mm, etc.

Referring again to the cap concave indentations (120, 220), the concave indentations (120, 220) are generally hemi-elliptical in shape. They are not completely hemispherical—they are slightly shorter than complete hemispheres. This allows exposure of a portion of a spherical nucleus (105) between the concave indentations (120, 220) so as to allow rotation of the caps (110, 210) about the spherical nucleus (105) therein.

Referring again to the outer surfaces (115) of the caps (110, 210), the outer surfaces (115, 215) resemble the curved face of a semi-cylindrical shape, oriented along the longitudinal axis (e.g., from the first ends to the second ends) (FIG. 5A shows the longitudinal axis).

The mobile cage system of the present invention may be also used in a MIS transforaminal surgical approach. For example, the method may comprise positioning the patient in a prone position; making an incision (e.g., para midline longitudinal incision) over the appropriate facets of the desired identified vertebrae; performing a total or sub-total facetectomy, removing the appropriate facets and exposing the nerve root. The root is protected superiorly. An incision is made into the disc space through the annulus fibrosus in the floor of the foramen. A partial discectomy is performed in the disc space for oblique insertion of a collapsed mobile cage system (100). The collapsed mobile cage system (100) may be implanted as described herein. For example, reaming is used to create a channel (for oblique insertion) for accepting the mobile cage system (100). Reaming retains at least a portion of the end plate of the two vertebrae.

The mobile cage system (100) is inserted in the channel in a collapsed position, and the nucleus (105) is inserted between the concave indentations (120, 220) of the caps (110, 210) by distracting the mobile cage (100), cradling the nucleus (105) in between the loading indentations (160, 260), pushing the nucleus (105) into the concave indentations (120, 220) of the caps (110, 220), and removing distraction so the nucleus (105) is captured by compression. The nucleus (105) separates the first cap inner surface (114) from the second cap inner surface (214) a certain distance and allows for motion of at least one cap (110, 210) relative to itself. After the nucleus is in place, the patient is closed.

Since rotation is through the articulation of the concavity, the oblique orientation of the system does not interfere with motion preservation. The transforaminal MIS approach may be used for appropriate circumstances, e.g., in patients with degenerative disc disease, scoliosis or other deformities, etc.

Nucleus

A nucleus (105) is housed (sandwiched) between the caps (110, 210) in the cavity (125) formed by the indentations (120, 220) of the caps (110, 210). The nucleus (105) helps provide stability and helps allow for mobility. Referring to FIG. 10, in certain embodiments, the nucleus (105) is spherical. In certain embodiments, the nucleus is ellipsoidal (and the concave indentations are shaped appropriately to form an ellipsoidal-shaped cavity.

The nucleus (105) of the mobile cage system (100) of the present invention may be constructed in a variety of sizes (e.g., to accommodate varying sizes of patients) and from a variety of materials. The system (100) is designed with sizes to allow for containment of the nucleus (105) in the cavity (125).

In certain embodiments, the nucleus (105) has a diameter of 10 mm (radius of 5 mm). In certain embodiments, the nucleus (105) has a diameter of 11 mm (radius of 5.5 mm). In certain embodiments, the nucleus (105) has a diameter of 12 mm (radius of 6 mm). In certain embodiments, the nucleus (105) has a diameter of 13 mm. In certain embodiments, the nucleus (105) has a diameter of 14 mm (radius of 7 mm). In certain embodiments, the nucleus (105) has a diameter of 15 mm. In certain embodiments, the nucleus (105) has a diameter of 16 mm (radius of 8 mm). In certain embodiments, the nucleus (105) has a diameter of 17 mm. In certain embodiments, the nucleus (105) has a diameter of 18 mm (radius of 9 mm). In certain embodiments, the nucleus (105) has a diameter of 19 mm. In certain embodiments, the nucleus (105) has a diameter of 20 mm (radius of 10 mm). In certain embodiments, the nucleus (105) has a diameter of 21 mm. In certain embodiments, the nucleus (105) has a diameter of 22 mm. In certain embodiments, the nucleus (105) has a diameter of 23 mm. In certain embodiments, the nucleus (105) has a diameter of 24 mm. In certain embodiments, the nucleus (105) has a diameter of 25 mm. In certain embodiments, the nucleus (105) has a diameter less than 10 mm. In certain embodiments, the nucleus (105) has a diameter greater than 10 mm.

In certain embodiments, the nucleus (105) has a diameter from 10 to 18 mm. In certain embodiments, the nucleus (105) has a diameter from 12 to 18 mm. In certain embodiments, the nucleus (105) has a diameter from 12 to 20 mm. In certain embodiments, the nucleus (105) has a diameter from 15 to 18 mm. In certain embodiments, the nucleus (105) has a diameter from 15 to 20 mm. In certain embodiments, the nucleus (105) has a diameter from 12 to 22 mm. In certain embodiments, the nucleus (105) has a diameter from 16 to 22 mm. In certain embodiments, the nucleus (105) has a diameter from 15 to 25 mm. In certain embodiments, the nucleus (105) has a diameter from 17 to 18 mm. In certain embodiments, the nucleus (105) has a diameter from 17 to 19 mm. In certain embodiments, the nucleus (105) has a diameter from 18 to 19 mm. In certain embodiments, the nucleus (105) has a diameter from 18 to 20 mm.

In some embodiments, the nucleus (105) is constructed from a high-density material, e.g., ultra high molecule weight polyethylene (UHMPE), high-density polyethylene (HDP), etc. The present invention is not limited to UHMPE or HDP. In certain embodiments, the nucleus (105) is constructed from a material comprising a material for adding stability and/or reducing wear and tear. In some embodiments, the nucleus (105) comprises a coating or outer layer for added stability and/or for reducing wear and tear. In certain embodiments, the material that adds stability and/or reduces wear and tear (e.g., a coating or outer layer, a material infused in the nucleus, etc.) comprises a cross-linked polyethylene material. In certain embodiments, the material that adds stability and/or reduces wear and tear (e.g., a coating or outer layer, a material infused in the nucleus, etc.) comprises vitamin E. See, for example, Shareghi et al. (J Bone Joint Surg Am, 2017, 99:1447-52), which features the study of Vitamin E-infused highly cross-linked polyethylene. In certain embodiments, the nucleus comprises a component (e.g., polymers) cross-linked Vitamin E. In certain embodiments, the nucleus is infused with Vitamin E. In certain embodiments, the nucleus is constructed from a material comprising a component (e.g., polymers) cross-linked with Vitamin E. In certain embodiments, the nucleus is coated with a component (e.g., polymers) cross-linked with Vitamin E. In certain embodiments, the nucleus is lined with a component (e.g., polymers) cross-liked with Vitamin E, etc. In certain embodiments, Vitamin E is introduced into polyethylene by blending with the component (e.g., polymer, e.g., polyethylene), e.g., a powder, before consolidation. In certain embodiments, Vitamin E is introduced into the component (e.g., polymer, e.g., polyethylene) by diffusion, e.g., after the irradiation.

In some embodiments, a marker is disposed in or on (e.g., around) the nucleus (105) allowing for visualization of the nucleus (105) using x-rays or other techniques. The marker may be constructed from a variety of materials such as but not limited to a metal or metal alloy. The present invention is not limited to the use of a marker. For example, following implantation, the x-ray can be used to measure the distance between the two caps to determine if the appropriate amount of space is present (the space corresponds to the presence of the nucleus).

As previously discussed, in certain embodiments, all or portions of the inner surfaces of the caps (110, 210), e.g., the concave indentations (120, 220), may be constructed from material comprising a metal, e.g., cobalt chromium, coated cobalt chromium, titanium, etc. and the nucleus (105) is constructed from a material comprising ultra high molecular weight polyethylene (UHMPE). Alternatively, in certain embodiments, all or portions of the inner surfaces of the caps (110, 210), e.g., the concave indentations (120, 220), may be constructed from material comprising ultra high molecular weight polyethylene (UHMPE) and the nucleus (105) is constructed from a metal, e.g., cobalt chromium, coated cobalt chromium, titanium, etc.

Without wishing to limit the present invention to any theory or mechanism, in certain embodiments, a two-piece configuration may be used in certain cases, such as a cervical disc replacement. For example, in certain embodiments, the nucleus (105) is fused to one of the concave indentations (120, 220). In certain embodiments, the nucleus (105) and one of the caps (110 or 120) are a single piece, wherein the opposing cap can rotate about the nucleus (105).

Methods of Use

The mobile cage system of the present invention is used to restore motion kinematics of the spine and may be inserted via a posterior or lateral approach into an intervertebral disc space, e.g., a disc space in the lumbar/sacral spine, a disc space in the cervical spine, etc.

The present invention features methods of treating degenerative disc disease, spinal stenosis, or other similar spinal conditions using the mobile cage system (100) of the present invention. The present invention also features methods of restoring motion kinematics of the spine using a mobile cage system herein. The present invention also features methods of replacing a L1-L2 disc, a L2-L3 disc, a L3-L4 disc, a L4-L5 disc, and/or a L5-S1 disc with a mobile cage system (100) of the present invention.

As an example, the mobile cage system (100) of the present invention may be placed posteriorly and via a minimally invasive technique (e.g., as compared to spinal fusions that require major anterior transabdominal surgery). The procedure to implant the mobile cage system is similar, yet simpler than a PLIF procure. It is less invasive than a PLIF and also allows motion between the two vertebrae.

In certain embodiments, the methods of replacing an intervertebral disc (e.g., for treating degenerative disc disease, spinal stenosis, etc.) may comprise retraction of the cauda equina, separation of the vertebrae, and removal of the disc between the two vertebrae.

The methods may further comprise shaving the vertebral end plates of the vertebrae using a reamer in the disc space. For example, a portion of the superficial layer (e.g., cartilage) of the vertebral end plate is shaved. (Note the rigid cages used for spinal fusion surgeries generally remove all of the vertebral end plate.) Retention of at least a portion of the vertebral end plate may be beneficial for bone growth. In some embodiments, reaming retains from 1 to 25% of the vertebral end plate. In some embodiments, reaming retains from 5 to 25% of the vertebral end plate. In some embodiments, reaming retains from 5 to 50% of the vertebral end plate. In some embodiments, reaming retains from 10 to 50% of the vertebral end plate. In some embodiments, reaming retains from 20 to 60% of the vertebral end plate. In some embodiments, reaming retains from 25 to 75% of the vertebral end plate. In some embodiments, reaming retains from 50 to 75% of the vertebral end plate. In some embodiments, reaming retains from 30 to 90% of the vertebral end plate.

In certain embodiments, the reamer may shave the vertebral end plate in a tubal fashion. An appropriately shaped reamer is used to allow for insertion of the system (100). For example, cylindrical reamer is used for a cylindrical-shaped system, a box-shaped reamer is used for a box-shaped system, etc. In some embodiments, a static reamer is used. In some embodiments, an expanding reamer is used. In some embodiments, from 0.25 to 0.5 mm is shaved from one or both of the vertebral end plates. In some embodiments, from 0.5 to 1.0 mm is shaved from one or both of the vertebral end plates. In some embodiments, 0.5 to 1.5 mm is shaved from one or both of the vertebral end plates. In some embodiments, 1.0 to 1.5 mm is shaved from one or both of the vertebral end plates. In some embodiments, 0.5 to 2 mm is shaved from one or both of the vertebral end plates. In some embodiments, 1.5 to 2.5 mm is shaved from one or both of the vertebral end plates.

The size of the reamer is chosen based on the size of the system. In certain embodiments, the reamer is a 16 mm reamer, a 14 mm reamer, a 12 mm reamer, a 10 mm reamer, etc.

The methods may further comprise insertion of one or two mobile cage systems (100) of the present invention into the intervertebral space. In certain embodiments, the caps (110, 210) are inserted in the collapsed position first, followed by insertion of the nucleus (105) between the caps (110, 210). In certain embodiments, the caps (110, 210) and nucleus (105) are inserted as a single piece (all-in-one insertion). The caps may be tapped into the intervertebral space with a particular surgical tool. In certain embodiments, a single mobile cage system is used. In certain embodiments, two mobile cage systems are used (see, for example, bi-lateral implantation in FIG. 12A).

In the case of inserting two mobile cage systems, the two cages (e.g., the outer edges, edges of the ridges, etc.) are separated a certain distance. For the purposes of orientation, for example, when viewing (from above, without the nucleus, etc.) a pair of first caps (110) that are both embedded into the vertebra, the two first caps are separated such that a space exists between the ridges (or outer edge) of the first caps such that the two first caps are not in contact. In certain embodiments, the cages are separated a distance of 2 mm. In certain embodiments, the cages are separated a distance of 3 mm. In certain embodiments, the cages are separated a distance of 4 mm. In certain embodiments, the cages are separated a distance of 5 mm. In certain embodiments, the cages are separated a distance of 6 mm. In certain embodiments, the cages are separated a distance of 7 mm. In certain embodiments, the cages are separated a distance of 8 mm. In certain embodiments, the cages are separated a distance of 9 mm. In certain embodiments, the cages are separated a distance of 10 mm. In certain embodiments, the cages are separated a distance of 11 mm. In certain embodiments, the cages are separated a distance of 12 mm. In certain embodiments, the cages are separated a distance of 13 mm. In certain embodiments, the cages are separated a distance of 14 mm. In certain embodiments, the cages are separated a distance of 15 mm.

In certain embodiments, the cages are separated a distance from 5 to 8 mm. In certain embodiments, the cages are separated a distance from 6 to 8 mm. In certain embodiments, the cages are separated a distance from 3 to 10 mm. In certain embodiments, the cages are separated a distance from 5 to 10 mm. In certain embodiments, the cages are separated a distance from 7 to 10 mm. In certain embodiments, the cages are separated a distance from 5 to 15 mm. In certain embodiments, the cages are separated a distance from 7 to 15 mm. In certain embodiments, the cages are separated a distance from 10 to 15 mm.

In some embodiments, the method comprises spreading the caps (110, 210) of the system (100) apart a particular distance. This may be achieved using a spreader (e.g., a bougie-type spreader). The spreading of the caps (110, 210) may help push the caps (110, 210) into the vertebral surface. The spreading of the caps (110, 210) may also allow for easier insertion of the nucleus (105) between the caps (110, 210).

The nucleus (105) may then be inserted or tapped between the end plates. As previously discussed, the nucleus may be constructed in a variety of shapes and sizes (e.g., spherical with a circular cross section, ellipsoidal with an oval cross section, rounded with tapered ends, etc.). A particular shape and/or size may be chosen depending on the height and weight of the patient.

Special instruments may be used to aid insertion of the caps (110, 210) and/or nucleus (105). For example, as discussed above, once the caps (110, 210) are in place in the intervertebral space, the caps may be separated by a spreader (serial spreader). The spreader may be designed with a material that does not scratch the caps (110, 210) or other components of the system (100). The spreader may spread the caps (110, 210) parallel to each other. In certain embodiments, a pushing instrument is used to push the nucleus (105) into the cavity (125). In certain embodiments, the pushing instrument has a concave indentation adapted to cradle the nucleus. In certain embodiments, once the nucleus (105) is inserted between the caps, tension is removed and an x-ray is taken to check placement of the system.

In some embodiments, the system (100) of the present invention is countersunk into the vertebral space, e.g., the system is not flush with the vertebrae and is not extending outwardly from the vertebrae. In some embodiments, the end of the system (100) is countersunk from 1 to 5 mm. In some embodiments, the end of the system (100) is countersunk from 2 to 4 mm. In some embodiments, the end of the system (100) is countersunk from 2 to 6 mm. In some embodiments, the end of the system (100) is countersunk from 3 to 7 mm. In some embodiments, the end of the system (100) is countersunk from 4 to 6 mm.

As an example of a posterior midline lumbar surgical approach featuring the system of the present invention, FIG. 12A shows a posterior-anterior view of the lumbar/sacral spine showing posterior midline placement of two mobile cages in the L4-5 space. FIG. 12B shows the side view of the spine in FIG. 12A.

As another example of a surgical approach featuring the system of the present invention, FIG. 13 shows a lateral TLIF approach (e.g., minimally invasive surgery) to insertion of a single mobile cage in both the L4-L5 and L5-S1 spaces. The view shown in FIG. 13 is an intermediate stage in the surgical procedure, e.g., after implantation of the mobile cage in the intervertebral space and prior to insertion of a nucleus between the two caps (110, 210). Flexion-extension of spine in this configuration may occur as a result of rocking barrel roll motion.

As previously discussed, in certain embodiments, the methods and systems of the present invention are used in the cervical spine. FIG. 14A and FIG. 14B show a surgical approach for applications involving the cervical spine. FIG. 14A shows an anterior-posterior view of C5-C6 with placement of a single mobile cage in the disc space. FIG. 14B shows a lateral view of the C6-C6 space (of FIG. 14A) with front to back placement of a single mobile cage. Note that the size and shape of the mobile cage used may depend on the location of insertion. For example, in some embodiments, the length and diameter of a mobile cage system used for cervical spine insertion may be from 12-14 mm.

Without wishing to limit the present invention to any theory or mechanism, because there are many different options for locations of insertions (e.g., cervical spine vertebrae, lumbar/sacral spine vertebrae) and types of surgical approaches (e.g., anterior approach for front to back insertion of a mobile cage system in a cervical spine space shown in FIG. 14A and FIG. 14B; minimally invasive spinal surgery (e.g., TLIF/lateral) insertion of a single mobile cage system from the side shown, posterior insertion of two mobile cage systems in a lumbar/sacral spine space shown in FIG. 12A, etc.), there may be many size (and shape) variations of the mobile cage system of the present invention.

Other instruments may be used for the methods of the present invention. Non-limiting examples include a scissor jack distractor and a vertebral body impactor. In some embodiments, the method of the present invention features the use of a light system, e.g., a fiber optic light, for visualization of one or more of the steps of the procedure. For example, a light system (e.g., fiber optic light) may be used to determine how much of the vertebral end plate is retained after reaming or whether or not the vertebral disc has been adequately removed and cleaned away.

As an alternative embodiment, in certain embodiments, the caps of the mobile cage system may be modified such that the loading indentations and portions of the concave indentations are absent so that when the caps are in the collapsed position a hollow channel is present and the nucleus (e.g., spherical nucleus) can be more easily pushed or slid into a modified cavity (e.g., the modified cavity being the remaining portions of the concave indentations). When the nucleus (e.g., spherical nucleus) is inserted through the hollow channel to the modified cavity, the caps separate a distance apart similar to how the caps in the aforementioned embodiments separate. A barrier can then be attached to each cap, e.g., a barrier to prevent the nucleus from exiting the cavity formed by the cages. The end result of the alternative embodiment is similar to the aforementioned embodiment, e.g., the caps are separated by the nucleus and the caps can rotate about the nucleus to restore motion kinematics of the spine.

EXAMPLE

The following example describes a surgical procedure for implantation of a mobile cage system of the present invention that may be performed by an orthopedic surgeon. The present invention is not limited to the method described herein.

The surgeon performs a decompression. To do so, the patient is laid prone on a carbon fiber deck. A mid-line incision is made directly over the spinous processes. Muscles are cleared from both sides, as far lateral as is essential. Retraction takes place to start the lam inectomy, which is the removal of the lamina (removing of the "roof" of the spine). Laminectomy may include bi-lateral hemi-laminectomy, bi-lateral partial facetectomy, or bi-lateral foraminotomy.

Next the surgeon puts in in the pedicle screws between the two vertebrae where mobile cage is to be installed. Then, a distractor is put in to open up the collapsed disc. The surgeon performs a partial or total discectomy as needed.

Next the surgeon relaxes the distraction and reams a single channel for the mobile cage system (100) centered on the interface between the two vertebrae.

For a mobile cage system (100), there is no need to pack bone in the cage. The mobile cage system (100) is porous coated to encourage bone growth with the upper and lower caps to gain stability. The system (100) is placed in the reamed well using an insertion tool, creating an interference fit which holds the upper and lower caps in place while bone growth occurs. After placement of the two mobile cages, the upper and lower halves of the mobile cage are distracted using a specialized tool and the nucleus is then placed. Distraction is removed and the nucleus is captured by the tension created by the anatomy of the body.

Next, the pedicle screws are removed. Then the patient is closed and the surgery is complete.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A mobile cage system (100) for posterior or lateral insertion in an intervertebral disc space, said system (100) comprising a pair of opposing caps, the pair of opposing caps comprising:

a. a first cap (110) having
      a first cap first end (111), a first cap second end (112) opposite the first cap first end (111), a first cap inner surface (114), and a first cap outer surface (115), the first cap outer surface (115) is a curved face of a semi-cylindrical shape oriented along a longitudinal axis, wherein at least a portion of the first cap outer surface (115) is porous;
      a first cap concave indentation (120) disposed in the first cap inner surface (114), the first cap concave indentation (120) is partial-hemispherical or partial-ellipsoidal, the first cap concave indentation (120) is for accepting a spherical nucleus that can rotate therein;
      a first cap loading indentation (160) disposed in the first cap inner surface (114), the first cap loading indentation (160) has a first end (161) at the first cap second end (112) and extends to a second end (162) near the first cap concave indentation (120), the first cap loading indentation (160) has a non-cylindrical shape in a form of a quarter ellipsoid wherein the first end (161) of the first cap loading indentation (160) has a width that is larger than that of the second end (162); and
      a first peak (170) disposed between the first cap concave indentation (120) and the second end (162) of the first cap loading indentation (160), the first peak (170) is a raised surface relative to a depth of the first cap concave indentation (120) and a depth of the first cap loading indentation (160), the first peak (170) prevents the spherical nucleus positioned in the first cap concave indentation (120) from being dislodged via the first cap loading indentation (160); and b. a second cap (210) having a second cap first end (211), a second cap second end (212) opposite the second cap first end (211), a second cap inner surface (214), and a second cap outer surface (215), the second cap outer surface (215) is a curved face of a semi-cylindrical shape oriented along a longitudinal axis, wherein at least a portion of the second cap outer surface (215) is porous;

a second cap concave indentation (220) disposed in the second cap inner surface (214), the second cap concave indentation (220) is partial-hemispherical or partial-ellipsoidal, the second cap concave indentation (220) is for accepting the spherical nucleus that can rotate therein;

a second cap loading indentation (260) disposed in the second cap inner surface (214), the second cap loading indentation (260) has a first end (161) at the first cap second end (112) and extends to a second end (162) near the second cap concave indentation (220), the second cap loading indentation (260) has a non-cylindrical shape in a form of a quarter ellipsoid wherein the first end (261) of the second cap loading indentation (260) has a width that is larger than that of the second end (262); and a second peak (270) disposed between the second cap concave indentation (220) and the second end (262) of the second cap loading indentation (260), the second peak (270) is a raised surface relative to a depth of the second cap concave indentation (220) and a depth of the second cap loading indentation (260), the second peak (270) prevents the spherical nucleus positioned in the second cap concave indentation (220) from being dislodged via the second cap loading indentation (260); and wherein the pair of caps can move between (i) a collapsed position for insertion into the intervertebral disc space via the posterior or lateral surgical method and (ii) a distracted position for insertion of the spherical nucleus between the concave indentations (120, 220);

wherein in the collapsed position the first cap inner surface is in contact with the second cap inner surface and the loading indentations together form a hemi-ellipsoid cavity, and in the distracted position the inner surfaces (114, 214) of the caps (110, 210) are a distance apart so that the loading indentations (160, 260) form a cradle and can temporarily hold and align the spherical nucleus for the purpose of inserting the spherical nucleus in between the concave indentations (120, 220).

2. The system (100) of claim 1, wherein the first peak (170) has a top edge (171) that is on a same plane as a top edge (125) of the first cap concave indentation (120).

3. The system (100) of claim 1, wherein the second peak (270) has a top edge (271) that is on a same plane as a top edge (225) of the second cap concave indentation (220).

4. The system (100) of claim 1, wherein the first peak (170) has a top edge (171) that is on a same plane as the first cap inner surface (114).

5. The system (100) of claim 1, wherein the second peak (270) has a top edge (271) that is on a same plane as the second cap inner surface (214).

6. The system (100) of claim 1, wherein the first cap concave indentation (120) and the second cap concave indentation (220) are hemi-elliptical in shape.

7. The system (100) of claim 1, wherein the first cap concave indentation (120) and the second cap concave indentation (220) are not complete hemispherical indentations to allow exposure of a portion of the spherical nucleus (105) therein between the concave indentations (120, 220) and to allow rotation of the caps (110, 210) about the spherical nucleus (105) therein.

8. The system (100) of claim 1 further comprising a first cap ridge (150) disposed along at least a portion of the first cap outer surface (115) of the first cap (110) and a second cap ridge (250) disposed along at least a portion of the second cap outer surface (215) of the second cap (210), the ridges (150, 250) function to prevent subsidence of the caps (110, 210).

9. The system (100) of claim 7, wherein the first cap ridge (150) is flush with the first cap inner surface (114) of the first cap (110), and the second cap ridge (250) is flush with the second cap inner surface (214) of the second cap (210).

10. The system (100) of claim 1, wherein the system (100) further comprises an attachment mechanism for temporarily securing the caps (110, 210) in the collapsed position.

11. The system (100) of claim 3, wherein the attachment mechanism comprises a peg disposed on the first cap inner surface (114) of the first cap (110) and an opposing hole disposed on the second cap inner surface (214) of the second cap (210), wherein the peg and the hole engage when the caps are in the collapsed position.

12. The system (100) of claim 3, wherein the attachment mechanism comprises bone wax disposed on the first cap inner surface (114) and the second cap inner surface (214).

13. The system (100) of claim 1 further comprising a first cap connecting component (130) disposed on the first cap second end (112) of the first cap (110) and a second cap connecting component (230) disposed on the second cap second end (212) of the second cap (210), the first cap connecting component (130) is shaped to engage a surgical tool that hold the caps (110, 210) together in the collapsed position.

* * * * *